(12) United States Patent
Sherman (10) Patent No.: US 8,403,899 B2
(45) Date of Patent: Mar. 26, 2013

(54) MAGGOT DEBRIDEMENT THERAPY DRESSINGS AND METHODS

(75) Inventor: Ronald A. Sherman, Irvine, CA (US)

(73) Assignee: Monarch Labs LLC, Irvine, CA (US)

( * ) Notice: Subject to any disclaimer, the term of this patent is extended or adjusted under 35 U.S.C. 154(b) by 643 days.

(21) Appl. No.: 12/498,318

(22) Filed: Jul. 6, 2009

(65) Prior Publication Data

US 2010/0010458 A1    Jan. 14, 2010

Related U.S. Application Data

(60) Provisional application No. 61/079,087, filed on Jul. 8, 2008.

(51) Int. Cl.
*A61M 1/00* (2006.01)
(52) U.S. Cl. .................. 604/304; 602/41; 604/298
(58) Field of Classification Search ............ 602/41, 602/42, 45, 52, 54, 59; 604/304, 305, 307, 604/313
See application file for complete search history.

(56) References Cited

U.S. PATENT DOCUMENTS

| | | | |
|---|---|---|---|
| 5,994,613 | A | 11/1999 | Cummings et al. |
| 6,359,189 | B1 | 3/2002 | Fleischmann |
| 6,555,729 | B1 | 4/2003 | Fleischmann |
| 6,557,487 | B1 | 5/2003 | Fleischmann |
| 6,770,794 | B2 | 8/2004 | Fleischmann |
| 6,863,022 | B2 | 3/2005 | Fleischmann |
| 6,875,907 | B2 | 4/2005 | Simmons et al. |
| 6,911,577 | B2 | 6/2005 | Simmons et al. |
| 7,723,559 | B2 * | 5/2010 | Linnane et al. ............ 602/42 |
| 2003/0124199 | A1 | 7/2003 | Nietsch et al. |
| 2003/0149388 | A1 | 8/2003 | Fleischmann |
| 2005/0123590 | A1 * | 6/2005 | Burton et al. ............ 424/445 |
| 2005/0277578 | A1 | 12/2005 | Leonard |
| 2007/0022960 | A1 | 2/2007 | Fleischmann |
| 2007/0142761 | A1 | 6/2007 | Aili |
| 2007/0161938 | A1 | 7/2007 | Aili |
| 2007/0191754 | A1 | 8/2007 | Aili |
| 2008/0102106 | A1 | 5/2008 | D'Haese et al. |
| 2009/0082710 | A1 * | 3/2009 | Vitaris ..................... 602/52 |
| 2010/0092439 | A1 | 4/2010 | Sherman |

FOREIGN PATENT DOCUMENTS

| | | | |
|---|---|---|---|
| WO | WO 0203898 A1 * | 1/2002 | |
| WO | WO 2010/005910 | 1/2010 | |
| WO | WO 2010/011611 | 1/2010 | |

OTHER PUBLICATIONS

Sherman, Ronald A., "A New Dressing Design for Use with Maggot Therapy", Plast Reconstructive Surg. 100 (2): 451-456, 1997.*
Duoderm (TM) dressing info, http://www.convatec.com/en/cvtus-productsus.*
Mesh Size to Aperture size conversion chart.*
Ackerman, Todd, "Maggots wriggling back into doctors' favor" Houston Chronicle Aug. 21, 2004.
Ahram, El, "The Larvae of the Bow Fly for treating diabetic foot ulcers," Medicine and Science, Tuesday, Mar. 28, 2006, pp. 34.
AP Maggot Article in Chinese, Aug. 2004.
Armstong, et al., "Letter to the editor : Maggot therapy in "lower-extremity hospice" wound care. Author's Response," J Am Podiatr Med Assoc. Jan.-Feb. 2006;96(1) 83.

(Continued)

*Primary Examiner* — Melanie Hand
(74) *Attorney, Agent, or Firm* — Grant Anderson LLP (57) ABSTRACT

Maggot debridement therapy dressing embodiments and methods are discussed for the treatment of a variety of indications including wound care, including septic wound care and the like.

28 Claims, 6 Drawing Sheets

OTHER PUBLICATIONS

Armstrong et al., "Maggot Therapy in "Lower-Extremity Hospice" Wound Care, Fewer Amputations and More Antibiotic-Free Days," Journal of the American Podiatric Medical Association, May/Jun. 2005, vol. 95, No. 3, pp. 254-257.
Attinger et al., "Clinical Approach to Wounds: Debridement and wound bed preparation including the use of dressings and Wound-Healing Adjuvants," vol. 117, No. 7S, Plastic and Reconstructive Surgery, June Supplement 2006, 72S-109S.
Baer et al., The treatment of chronic osteomyelitis with the maggot (Larva of the Bow Fly), 438-475.
Baer, William S., "Sacro-Iliac Joint-Arthritis Deformans Viable Antisceptic in Chronic Osteomyelitis," Oct. 25, 1929, 1929 Proceedings, Inter-State Postgraduate Medical Assembly of North America, pp. 365-372.
Baker, John, "Maggot Therapy Re-Emerging, Fly Larvae doing 'Grub'—by Jobs, Treatment in Napolean's Army Shows Promise in Treatment of Diabetes-Related Wounds, Diabetes Interview, Kings Publishing, Issue 34, May 1995.
Balock, "Grubby little secret: Maggots are neat at fighting infection," The Wall Street Journal, Tuesday Jan. 17, 1995, vol. CXXXII No. 11, Western Edition.
Beasley et al., "Making a meal of MRSA—the role of biosurgery in hospital-acquired infection," Journal of Hospital Infection (2004) 56, 6-9.
Bell, et al., "Use of Sterile Maggots to treat panniculitis in an aged donkey," The Veterinary Record, Dec. 22/29, 2001, pp. 768-770.
Bexfield et al., "The antibacterial activity against MRSA strains and other bacteria of a <500 Da fraction from maggot excretions/secretions of *Lucilia sericata* (Diptera: Calliphoridae)," Microbes and Infection (2008) 1-10.
Bexfield, et al., "Detection and partial characterisation of two antibacterial factors from the excretions/secretions of the medicinal maggot *Lucilia sericata* and their activity against methicillin-resistant *Staphylococcus aureus*(MRSA)," Microbes and Infection, 6(2004) 1297-1304.
Blake et al., "The biosurgical wound debridement: Experimental investigation of efficiency and practicability," Wound Repair and Regeneration, (2007) 15, pp. 756-761.
Bonn, Dorthy, "Maggot Therapy: an alternative for wound infection," The Lancet, vol. 356, Sep. 30, 2000, pp. 1174.
Bowling et al., "Larval Therapy in the Treatment of diabetic food wounds," EWMA Journal 2008, vol. 8, No. 1, pp. 10-16.
Bowling et al., "Larval Therapy: A Novel Treatment in Eliminating Methicillin-Resistant *Staphylococcus aureus* From Diabetic Foot Ulcers," Diabetes Care, vol. 30, No. 2 Feb. 2007, pp. 370-371.
Brander et al., "An Ex-vivo Model to Evaluate Dressings & Drugs for Wound Healing," EWMA Journal, 2006, vol. 6, No. 2, 11-15.
Brem et al., "Protocl for the successful treatment of pressure ulcers," The American Journal of Surgery, 188 (Supp to Jul. 2004) 9S-17S.
Broughton et al., "A Brief History of Wound Care," Plastic and Reconstructive Surgery, June Supplement 2006, pp. 7S-11S.
Broughton et al., "The Basic Science of Wound Healing," Plastic and Reconstructive Surgery, June Supplement 2006, 12s-34s.
Broughton et al., "Wound Healing: An overview," Plastic and Reconstructive Surgery, June Supplement 2006, pp. 1eS-32e5.
BTER Draft Policies and Procedures Template for Maggot Debridement Therapy, 2005.
Bunkis et al., "Maggot Therapy Revisited," The Western Journal of Medicine, Apr. 1985, 142(4), pp. 554-556.
Cadden, Sue, "Monthly Profile—Ronald A. Sherman, MD", Wound Expert Times by Net Health Systems, Inc. Nov. 2004.
Calianno C, Jakubek P. Wound bed preparation: laying the foundation for treating chronic wounds, part 1. Nursing. Feb. 2006;36(2):70-1.
Cambal M, Labas P, Kozanek M, Takac P, Krumpalova Z. Maggot debridement therapy. Bratisl Lek Listy. 2006;107(11-12):442-4.
Carlson, Bob, "Crawling through the millennia: Maggots and Leeches Come Full Circle," Diagnostics and Devices, Biotechnology Healthcare, Feb. 2006, pp. 14-17.
Carnie, Tony, "Nature's little surgeons, Doctors are increasingly using 'maggot therapy' to clean up non-healing wounds, especiall in patients with poor circulation or where there are antibiotic-resistant bugs," The Mercury, 12, Thursday Apr. 5, 2007.
Chan et al., "Maggot Debridement Therapy in chronic wound care," Review Article in: Hong Kong Med J, vol. 13, No. 5, Oct. 2007, pp. 382-386.
Chernin, Eli, "Surgical Maggots" Southern Medical Journal, Sep. 1986, vol. 79, No. 9, pp. 1143-1145.
Cheshier et al., "Cerebral Myiasis Associated with Angiosarcoma of the Scalp: Case Report," Neurosurgery vol. 61, No. 1, Jul. 2007, E167.
Church JC, Courtenay M. Maggot debridement for chronic wounds. Int J Low Extrem Wounds. Jun. 2002;1(2):129-134. Erratum in: Int J Low Extrem Wounds. Sep. 2002;1(3)213.
Church, John C.T., "Maggot Therapy, A handbook of maggot-assisted wound healing by Fleischmann and Sheman" Book Review in: Lower Extremeity Wounds 4(1);2005, p65.
Church, John C.T., Re: Bleeding Complications in Patients Treated With Maggot Debridement Therapy. Steenvord P. and Oskam J. IJLEW 2005;4(1):57-58 Letter to the Editor in: Lower Extremeity Wounds 4(1);2005, p59.
Claxton, M.J., "5 Questions-and answers about maggot debridement therapy," Advances in Skin and Wound Care, Mar./Apr. 2003, vol. 16, No. 2, pp. 99-102.
Contreras-Ruiz et al., "Maggot therapy and infection control in venous ulcers: a comparative study." Presented at: Symposium on Advanced Wound Care (SAWC); Apr. 21-24; San Diego, CA. 2005.
Contreras-Ruiz, et al., "Larval Debridement Therapy in Mexico," Wound Care Canada, vol. 3, No. 1, 2005, pp. 42-46.
Cowland, Greg, untitled paper on wound healing Dec. 2006, pp. 1-20.
Cronje et al., "Maggot Debridement Therapy, MDT in South Africa Today," Palmunt Post, 9-2, 2006.
Daeschlein, et al., "In vitro Antibacterial Activity of Lucilia sericata Maggot Secretions ," Skin Pharmacol. Physiol,., 2007, vol. 20, pp. 112-115.
Dang et al., "Changing Prespectives in Diabetic Foot Ulcer Management," Lower Extremety Wounds 2(1):2003 pp. 4-12.
Dente, Karen M., "Alternative Treatments for Wound: Leeches, Maggots, and Bees," Abkhazi Institute for Social and Economic Research, Friday 30, 2007.
Dixon, Major Oness, "The treatment of chronic osteomyelitis and other suppurlative infections with live maggots (Larva of the Bow Fly)." The Veterinary Bulletin, vol. 27, 1933, pp. 16-20.
Dreher, G.C., "Maggot Dentists" Time, Jul. 3, 1933, pp. 26.
Dunn C, Raghavan U, Pfleiderer AG. The use of maggots in head and neck necrotizing fasciitis. J Laryngol Otol. Jan. 2002;116(1):70-2.
Eldor et al., "New and experimental approaches to treatment of diabetic foot ulcers: a comprehensive review of emerging treatment strategies," Diabetics Medicine, 21 pp. 1161-1173.
Emsen et al., "Fatal side effect of maggot threatment on wound healing," Plastic and Reconstructive Surgery, Apr. 15, 2007, pp. 1624.
Evans, "Larvae therapy and venous leg ulcers: reducing the 'yuk factor'" Journal of Wound Care, vol. 11, No. 10, Nov. 2002, pp. 407-408.
Fadaak, "Letter to the editor in Burns," Burns 29 (2003) 96.
Fine et al., "Maggot Therapy, Technique and Clinical Application," Journal of Bone and Joint Surgery, 1934, vol. 16.
Fitzpatrick, Michael, "Tiny "Surgeons" Prove Surprisingly Effective," JAMA, Nov. 8, 2000, vol. 284, No. 18, pp. 2306-2307.
Fleischmann et al., "Boisurgery-Maggots, are they really the better surgeons?" Der Chiurg, 1999 (70)1340-1346.
Frykberg, "In Reply, Maggot Debridement therapy for Diabetic Necrotic Foot," Letter to the editor American Family Physcian, vol. 68, Iss. 12, Dec. 2003.
Galeano, et al., "Maggot Therapy for the treatment of osteomyelitis and deep wounds: an old remedy for an actual problem," Plast Reconstr Surg, vol. 108(7) Dec. 2002, pp. 2178-2179.
Gericke et al., "Maggot therapy following orbital extenteration," Br. J. Opthalmol. 2007;91 pp. 1715-1716.
Glinski, Mark, "Get Me 500 Maggots STAT, Maggot and leech therapy coming out of the woodwork," CMA Today, May/Jun. 2007, pp. 18-22.

Glod A. [An efficient method for managing problem wounds: maggot therapy in biosurgery] Pflege Z. Mar. 2007;60(3):131. German.
Goldstein, H.I., "Maggots in the treatment of wound and bone infections," Camden, NJ, 476-478.
Graniger et al., "Biosurgical Debridement facilitates Healing of Chronic Skin Ulcers," Arch Intern Med, vol. 162, Sep. 9, 2002, pp. 1906-1907.
Grassberger et al., "Effect of temperature on development of *Liopygia* (= Sarcophaga) *argyrostoma* (Robineau-Desvoidy) (Diptera: Sarcophagidae) and its forensic implications," J Forensic Sci. Nov. 2002;47(6):1332-1336.
Grassberger et al., "Effect of temperature on development of *Lucilia sericata* (Diptera: Calliphoridae) development with special reference to the isomegalen- and isomorphen-diagram," Forensic Sci.International 120, (2001) 32-36.
Grassberger et al., "Woundhealing by means of sterile fly larvae: Mechanical, Biochemical and Microbiological Basis," Wien. Med. Wschr. 2003; 153, pp. 198-201.
Greer, Kathleen A., "Age-old Therapy Gets New Approval," Advances in Skin and Wound Care, vol. 18, No. 1, pp. 12 and 15, Jan./Feb. 2005.
Grossman, Joel, "At the Edge, Flies as Medical Allies," Natural Science, pp. 187-193, Oct. 1994.
Gwynne B, Newton M. An overview of the common methodsof wound debridement. Br J Nurs. Oct. 26-Nov. 8, 2006;15(19):S4-S10. Review.
Harris, Gardiner, "Age-Old Cures, Like the Maggot Get U.S. Hearing," New York Times, Aug. 25, 2005.
Harvey et al., "Mitochondrial DNA cytochrome oxidase I gene: potential for distinction between immature stages of some forensically important fly species (Diptera) in western Australia," Forensic Science International, 131 (2003), 134-139.
Hewitt J.F., "Osteomyelitis, Development of the Use of Maggots in Treatment," Am. J. of Nursing, 32(1); pp. 31-38, (1932).
Hoke, Toria K., "Out with the new and in with the old," WOCN Course Jan. 15, 2008, pp. 1-22.
Horn et al., "Maggot Therapy for Subacute Mastoiditis," Arch Otolaryngol vol. 102, Jun. 1976, pp. 377-379.
Horobin et al., "Maggots and wound healing: an investigation of the effects of secretions from *Lucilia sericata* larvae upon interactions between human dermal fibroblasts and extracellular matrix components," British Journal of Dermatology 2003; 148, pp. 923-933.
Horobin et al., "Maggots and wound healing: an investigation of the effects of secretions from *Lucilia sericata* larvae upon the migration of human dermal fibroblasts over a fibronectincoated surface," Wound Rep Reg 2005; 13: 422-433.
Horobin et al., "Promotion of Human Dermal Fibroblast Migration, Matrix Remodelling and Modification of Fibroblast Morphology within a Novel 3D Model by *Lucilia sericata* Larval Secretions," Journal of Investigative Dermatology, (2006) vol. 126, pp. 1410-1418.
Hou et al., "Antibacterial activity in vitro anti-tumor activity of the extract of the larvae of the housefly (*Musca domestica*)," Journal of Ethnopharmacology, 111 (2007) 277-231.
Hoyle, Brian, "Maggot Extracts Disrupt Both Ghram-Negative and -Positive Bacterial Biofilms", Microbe, vol. 2, No. 7, 2007, pp. 331-332.
Huberman et al., "Antibacterial Substances of lo molecular weight isolated from the bowfly, *Lucilia sericata*," Medical and Veterinary Entomology (2007) 21, pp. 127-131.
Husain ZS, Fallat LM. Maggot therapy for wound debridement in a traumatic foot-deglovinf injury: a case report. J Foot Ankle Surg. Nov.-Dec. 2003:42(6):371-6.
International Search Report and Written Opinion Mailed on Feb. 24, 2010 in International Application PCT/US2009/051175 filed on Jul. 20, 2009 and published as: WO 10/011611 on Jan. 18, 2010.
International Search Report and Written Opinion Mailed on Jan. 20, 2010 in International Application PCT/US2009/049720 filed on Jul. 6, 2009 and published as: WO 10/005910 on Jan. 14, 2010.
Iverson, Eve, "Methods of Treating Injuries of Work Animals", Buffalo Bulletin (Jun. 1996) vol. 15, No. 2, pp. 34-37.
James C. Use of sterile maggots in an unusual trauma injury. Br J Nurs. Mar. 22-Apr. 11, 2007;16(6):S30-1.

Jarvis A. Maggot therapy. Lancet. Dec. 9, 2000;356(9246):2016.
Jones et al., "Maggot-therapy in veterinary medicine," Res Vet Sci (2008), pp. 394-398.
Jourdan, Martin, "Editorial, Larval Therapy," Int J Clin Pract, Mar. 2007, 61, 3, pp. 359-356.
Jukema et al., "Amputation-Sparing Treatment by Nature: "Surgical" Maggots Revisited," CID 2002:35 (Dec. 15, 2002) pp, 166-1571.
Jukema et al., "Maggot Therapy for Treatment of Severe Infections in Trauma Surgery: Back to the Future," Zentralbl Chir 2006, 131: pp. S73-S78.
Jurga et al., "Maggot Debridement Therapy, Alternative Therapy for Hoof Infection and Necrosis," Hoofcare and Lameness, Issue 78, pp. 28-31.
Kawabata, Takuya, "Induction of Antibacterial activity in medicinal maggots by infected environment," abstract from Seventh International Conference on Biotherapy, Jun. 21-27, 2007.
Keefe, Sandy, "Maggots and Leeches, Ancient treatments among modern interventions for wounds that won't heal," Advance for Nurses, Mar. 3, 2008, 27-28.
Kerridge et al., "Antibacterial properties of larval secretions of the blowfly, *Lucilia sericata*," Medical and Veterinary Entomology (2005) 19, 333-337.
Kirshen et al., "Debridement: A vital componenet of bed preparation," Advances in Skin & Wound Care, vol. 19, No. 9, Nov./Dec. 2006.
Kitching, M., "A phenomenological study investigating: Patient Perceptions and Experiences of Maggot Therapy," J. Wound Care, Jan. 2004, 13(1):25-29.
Knowles A, Findlow A, Jackson N. Management of a diabetic foot ulcer using larval therapy. Nurs Stand. Oct. 24-30, 2001;16(6):73-6.
Krajacic A. Consider using maggots. Todays Surg Nurse. May-Jun. 1998;20:28-32.
Kyodo, "Gangrene cure a free lunch for maggots," ABC News Online, Oct. 10, 2004.
Lalonde, Pati "Maggots or Miracles? Squirm factor is high, but there is no disputing centuries-old remedy for cleaning wounds," The Bay City Times, Section C, Health and Science, Tuesday, Jul. 19, 2005.
Lau et al., "Maggots in surgery," Ann. Coll Surg. (2000) 4, pp. 50-53.
Lau, H, "Maggots in ulcers: Friend or Foe?" HKJM vol. 6, No. 1, Mar. 2000, pp. 234.
Leclercq, M. "Utilisation de larves de Dipteres—Maggot Therapy—en medicine: historique et actualite," Bull. Annls Soc. R. beige Ent. 126(1990):41-50.
Lederle Labaoratories Product Literature, "Directions for using Surgical Maggots in Chronic Osteomyelitis and other Supportive Infections," JAMA, 98(5), 1932, pp. 20-21.
Lerch et al., "Bacteria Ingestion by Blowfly Larvae: An Invitro Study," Dermatology 2003; 207: pp. 362-366.
Leyva-Moral, J.M., "Efficacia de la terapia larval en el desbridamiento de heridas cronicas," Revision Bibliografica, Rev ROL Enf, 2007, 30(1).
Lipsky, B., "Adjunctive Therapies for Diabetic Foot Infections, Treatment Options that go beyond antibiotics may be needed to treat some diabetic foot infections," Diabetic Microvascluar Complications Today, Jul./Aug. 2005, pp. 22-24.
Lodge et al., "Maggots 'n' chips: a novel approach to the treatment of Diabetic ulcers," Wound Care, Dec. 2006, pp. S23-S24.
Long et al., "Wiggling Subcutaneous Lumps" Photo quiz and answer in CID Aug. 15, 2003.
Martin et al., "Maggot Debridement Therapy in the Treatment of Nonhealing Chronic Wounds," Proceedings of the 3rd Annual GRASP Symposium, Wichita State University 2007, pp. 133-134.
Martin et al., "Maggots and Osteomyelitis," 930-950, Ann Surg. Nov. 1932; 96(5): 930-950.
Martin, Dodie L., "Maggot Debridement Therapy in the Treatment of Nonhealing Chronic Wounds," Department of Physician Assistant and Graduate School of Wichita State University, May 2007.
Martini et al., "Terapia de Desbridamento com Larvas," JMB vol. 85, No. 4, Oct. 2003, pp. 82-85.
Masri et al., "Sterilisation of *Lucilia cuprina* Wiedmann maggots used in therapy of intractable wounds," Tropical Biomedicine 22(2): 185-189 (2005).

McKeever, D., "Maggots in Treatment of Osteomyelitis," Journal of Bone & Joint Surgery, 1933 vol. 15, pp. 85-93.

Millard, "Larva therapy: a case for inclusion in the Drug Tarrif," Nursing Times, Sep. 3, 2002, vol. 98, Issue 36, p. 48.

Miller-Cox, "Maggot Debridement Therapy in the Calciphylaxis Patient: Analysis of 4 cases," SWAC 2006.

Mitsui et al., "Wound Bed Preparation (WBP) by MDT (Maggot Debridement Therapy)," Abstracts from the 34th Annual Meeting od the Japanese Society for Wound Healing, Nov. 29-30, 2004, pp. A8.

Morrison, Scott E., "How to Use Sterile Maggot Debridement Therapy for Foot Infections of the Horse," AAEP Proceedings, vol. 51, 2005.

Morrison, Scott, "Foot Management," Clin Tech Equine Pract 3:71-82, 2004.

Mumcuoglu et al., "Maggot Therapy for the Treatment of TIntractable Wounds," International Journal of Dermatology, 1999, 36, pp. 623-627.

Mumcuoglu et al., "Maggot Therapy fot the Treatment of Diabetic Foot Ulcers," Diabetes Care, vol. 21, No. 11, Nov. 1998, 2030-2031.

Mumcuoglu KY, Miller J, Mumcuoglu M, Friger M, Tarshis M. Destruction of bacteria in the digestive tract of the maggot of *Lucilia sericata* (Diptera: Calliphoridae). J Med Entomol. Mar. 2001;38(2):161-6.

Mumcuoglu, Kosta T., "Clinical Applications for Maggots in Wound Care," Am J. Clin. Dermatolo,, 2001, 2(4), pp. 219-227.

Namias et al., "Biodebridement: A case report of maggot therapy for limb salvage after fourth-degree burns," J. Burn Care Rehabil, 2000, 21:254-257.

Neergaard, "Maggots make a medical comeback," Associated Press, Aug. 3, 2004.

Neergaard, Lauran, "Mini surgeons; Maggots make medical comeback for wound healing" Associated Press Aug. 16, 2004.

NGC Guideline, "Guideline for management of wounds in patients with lower-extremity venous disease," National Guideline Clearinghouse Jan. 7, 2008, pp. 1-14.

Nguyen, Hahh, et al., "Post Marketing Surveillance (Phase 4 Study) of medical Maggots Confirms Low Risk of Maggot Therapy," Abstract presented at Clinical Symposium on Advance in Sking and Wound Healing, Orlandon Florida, Sep. 2006.

Nigam et al., Maggot Therapy: The science and implication for CAM Part 1—History and Bacterial Resistance eCAM . 3(2) May 5, 2006, pp. 223-227.

Nigam Y, Bexfield A, Thomas S, Ratcliffe NA. Maggot therapy: The science and implication for CAM part II—Maggots Combat Infection. eCAM Advance Access published May 8, 2006.

Ochsenhirt, N.C. et al., "Treatment of Osteomyelitis of Mandible by intraoral Maggot Therapy.," International Association for Dental Research (IADR) Eleventh General Meeting Hotel Stevens, Chicago, Illinois Mar. 18 and 19, 1933, Abstract No. 104, pp. 245-255.

Orkiszewski, Marek et al., "The use of maggot therapy as an adjunct to surgical debridement: a paediatric case report," World Wide Wounds, Mar. 2006.

Parnes, et al., "Larval therapy in wound management: a review," J Clin Pract Mar. 2007, 61(3) 488-493.

Pearson, Christine "Something old is new again: Debriding and reducing local wound infection with maggots" Clinical Practice 5(2) 2007 22-26.

Petherick et al., "Patient acceptability of larva therapy for leg ulcer treatment: a randomized survey to inform the sample size calculation of a randomized trial," BMC Medical Research Methodology 2006, 6:43.

Picazo et al., "Sterile maggots as adjuvant procedure for local treatment in a patient with proximal calciphylaxis," Nefrologia 2005;25(5):559-562. Article in Spanish (abstract).

Piccolo, Cynthia M., "Creepy-Crawly Therapies, Remedies that suck, sting, and slither," Medhunters Magazine 44; 2002.

Pliquett et al., "Calciphylaxis in chronic, non-dialysis-dependent renal disease," BMC Nephrology, pp. 1-5, 2003.

Prete, Pamela E., Growth Effects of Phaenica Sericata Larval Extracts on Fibroblasts: Mechanism for Wound Healing by Maggot Therapy, Life Sciences, vol. 60, No. 8, pp. 505-510.

Preuss et al., "The successful use of maggots in necrotizing faciitis of the neck: a case report," Head & Neck, Aug. 2004, 747-750.

Risen, "Medical Maggots" New York Times Dec. 11, 2005.

Robinson et al., "The rol of surgical maggots in the disinfection of osteomyelitis and other infected wounds," Journal of Bone and Joint Surgery, 1933, vol. 15, pp. 409-412.

Rojo et al., "Notes on Practice: Hemophillia and Maggots: From Hospital Admission to healed Wonund," Ostomy Wound Management, vol. 50, issue 4, Apr. 2004, pp. 30-34.

Root-Bernstein et al., "Honey, Mud, Maggots, and other Medical Marvels, The Science Behind Folk Remedies and Old Wives' Tales" Chaper 2, A Flyblown Idea, Houghton Mifflin Company, 1997.

Rosato et al, Letters to the Editor in Plastic and Reconstructive Surgery, vol. 117, No. 5, Letters and Viewpoints, Apr. 15, 2006, pp. 1641-1671.

Rowland et al., "Medical Maggots make a Comeback," Wound Healing Perspectives, vol. 2, No. 2, Spring 2005, pp. 1-8.

Ryan, Terrance J., "Evans (1996) Exchange and the Skin in Light of Vacuum-Assisted Closure, Yoga and Maggots", Lower Extremity Wounds 3(3);2004 pp. 121-122.

Scavee V, Polis X, Schoevaerdts JC. Maggot therapy: many hands makelight work. Acta Chir Belg. Aug. 2003;103(4);405-7.

Schafter-Wishnor, "Larvae show medical promise," The Daily Cardinal, Science Section, Thursday Mar. 29, 2005, vol. 115, Issue 111.

Sealby N. The use of maggot therapy in the treatment of a malignant foot wound. Br J Community Nurs. Mar. 2004;9(3):S16-S19.

Semple L. Use of larval therapy to treat diabetic patient's pressure ulcer. Br J Nurs. Aug. 2003;12(15 Suppl):S6-13.

Sforza, Teri, "UCI doctor a believer in maggots' medical magic," The Orange County Register Sunday, Jun. 18, 2000.

Shapiro, Charles E. "Maggot Debridement Therapy (MDT), "Entemotherapy": Precision Use of an Age Old Technique" World Society for Microsurgery IV Congress; Athens Greece: Jun. 2007.

Sherman & Wyle, 1996 [Sherman RA and Wyle FA: Low-cost, low-maintenance rearing of maggots in hospitals, clinics, and schools. Am J Trop Med Hyg. 54 (1): 38-41. 1996.

Sherman et al, "Healthcare-Associated Myiasis Prevention and Intervention," Infection Control and Hospital Epidemiology, Oct. 2005 828-832.

Sherman et al., "Effects of Seven Antibiotic on the Growth and Development of *Phaenicia sericata* (Diptera: Calliphoridae) Larvae" Journal of Medical Entomology, Sep. 1995 646-649.

Sherman et al., "Letters to the Editor and Reply" Plastic and Reconstructive Surgery Nov. 2007.

Sherman et al., "Low-cost, low-maintenance rearing of maggots in hospitals, clinics, and schools," Am. J. Trop. Med Hyg., 54(1) 1996, pp. 38-41.

Sherman et al., "Maggot Debridement Therapy in Outpatients" Arch Phys Med Rehabil vol. 82, Sep. 2001, pp. 1226-1229.

Sherman et al., "Maggot debridement Threapy for serious horse wounds—a survey of practioners," The Veterinary Journal 174 (2007) 86-91.

Sherman et al., "Maggot Therapy fo treating pressure ulcers in spinal cord injury patients," The Journal of Spinal Cord Medicine 18(2) 71-74 (1995).

Sherman et al., "Maggot therapy for problematic wounds: Uncommon and Off-label Applications," Original Investigation, Advances in Skin & Wound Care, vol. 20, No. 11, pp. 602-610.

Sherman et al., "Maggot Therapy for Venous Stasis Ulcers," Dermatology, Mar. 1996, vol. 132, 254-256.

Sherman et al., Maggot Therapy Information Sheet for Physicians (FAQs) 2005.

Sherman et al., "Maggot Therapy: a review of the therapeudic applications of fly larvae in human medicine, especially for treating osteomyelitis," Medical and Veterinary Entomology (1988) 2, 225-230.

Sherman et al., "Medical Maggots; an ancient remedy for some contemporary afflictions," Annual Review of Entomology; 45:55-81, 2000.

Sherman et al., "Presurgical Maggot Debridement of Soft Tissue Wounds in Associated with Decreased Rates of Postoperative Infection," Brief Report Clinical Infectious Diseases, 2004:39 (Oct. 1, 2004) 1067-1070.

Sherman et al., "Survey of Off-Label Applications of Maggot Threapy", Abstract in Symposium on Clinical Advances in Skin and Wound Healing; Orlando, FL Sep. 2006.

Sherman et al., "Treating wounds in small animals with maggot debridement therapy: A survey of practitioners," The Veterinary Journal 173 (2007) 140-145.

Sherman et al., "Tuberculosis tracking: Determining the frequency of the booster effect in patients and staff," AJIC, vol. 29, No. 1, pp. 7-12.

Sherman et al., A simple steril food structure for rearing the larva of Lucilia sericata (Diptera: Calliphoridae) Medical and Vetrinary Entomology (1995) 9, 393-398.

Sherman R. Age-old therapy gets new approval. Adv Skin Wound Care. Jan.-Feb. 2005;18(1):12-5.

Sherman RA: Cohort study of maggot therapy for treating diabetic foot ulcers. Diabetes Care 2003; 26(2):446-51.

Sherman, "Maggots make medical comeback for healing wounds" Obesity, Fitness & Wellness Week, Aug. 28, 2004.

Sherman, "Larvatherapy" Program from: 1a Reunion International de Actualizacion en Cictrizacion y Manejo de Heridas Cronicas, Sep. 5-6 2003.

Sherman, "Maggot Therapy" APIC Newsletter (1995) vol. 6(3): p. 5.

Sherman, "Medicine, Insects in," Encyclopedia of Insects (2003), 698-700.

Sherman, et al., "Healthcare-Associated Myiasis: Prevention and Intervention," Review in Infection Control and Hospital Epidemiology, Oct. 2005, pp. 828-832.

Sherman, et al., "Maggot Therapy for Venous Stasis Ulcers," Archives of Dermatology vol. 132, Mar. 1996, pp. 254-256.

Sherman, R.A., "Creepy, crawly surgeons" Technology and Science by Weekly Reader, Aug. 18, 2005, pp. 178-179.

Sherman, R.A., "Maggot Debridement Therapy for Treating Non-Healing Wounds," Abstract on pp. 327, Wound Repair and Regeneration, vol. 8, No. 4, 2000.

Sherman, R.A., "Maggot versus conservative debridement therapy for the treatment of pressure ulcers," Wound Repair and Regeneration, Jul./Aug. 2002:10(4):208-214.

Sherman, Ronald A., "A New Dressing Design for Use with Maggot Therapy," Ideas and Innovations, Plastic and Reconstructive Surgery Aug. 1997, pp. 451-456.

Sherman, Ronald A., "Maggot Debridement in Modern Medicine" Infections in Medicine, Sep. 1998, 651-656.

Sherman, Ronald A., "Maggot Therapy for Foot and Leg Wounds," Lower Extremity Wounds 1(2); 2002 pp. 135-142.

Sherman, Ronald A., "Maggot Therapy for Treating Diabetic Foot Ulcers Unresponsive to Conventional Therapy," Diabetic Care, vol. 26, No. 2, Feb. 2003, pp. 446-451.

Sherman, Ronald A., "Putting Wild Maggots on Your Head is Not "Maggot Therapy," but it does suggest Pre-existing Pathology," Plastic and Reconstructive Surgery, Nov. 2007 1737-1748.

Sherman, Ronald, "Maggot Therapy", Orange County Register, Monday Oct. 10, 2005.

Sherman,"Maggot Therapy—The Last Five Years," European Tissue Repair Society, vol. 7, (3) 97-98.

Smith Ag, Powis RA, Pritchard DI, Britland ST. Greenbottle (Lucilia sericata) larval secretions delivered from a prototype hydrogel wound dressing accelerate the closure of model wounds. Biotechnol Prog. Nov.-Dec. 2006;22(6):1690-6.

Soddard et al., "Maggot Debridement Therapy, An Alternatice Treatment for Nonhealing Ulcers" Journal of the American Podiatric Medical Association, 85(4) Apr. 1995 218-221.

Sosin, Joan, "Ancient Remedy Heals Today's Wounds," Nursing Spectrum, Career Management Magazine Articles, Mar. 14, 2005.

Steenvoorde et al., "Maggot Debridement Therapy in Necrotizing Fasciitis Reduces the Number of Surgical Debridements," Wounds 2007; 19(3):73-78.

Steenvoorde et al., "Maggot debridement therapy of infected ulcers: patient and wound factors influencing outcome—a study on 101 patients with 117 wounds," Annals of the Royal College of Surgeons od England, vol. 89, No. 6, Sep. 2007 pp. 596-602 (7).

Steenvoorde et al., "Maggot-Treated wounds follow normal wound healing phases", Internation Jourlan of Dermatology, 2006, 45, 1477-1479.

Steenvoorde et al., "The Yuk Factor, Maggot debridement therapy: the ancient treatement for chronic wounds makes a comeback.," The Hospitalist, Aug. 2006, pp. 16-20.

Steenvoorde P, Buddingh TJ, van England A, Oskam J. Maggot therapy and the "yuk" factor: an issue for the patient? Wound Repair Regen. May-Jun. 2005;13(3)350-2.

Steenvoorde P, Jacobi CE, Oskam J. Letter to the editor : Maggot therapy in "lower-extremity hospice" wound care. J Am Podiatr Med Assoc. Jan.-Feb. 2006;96(1):82-83.

Steenvoorde P, Jukema GN. Can laboratoy investigations help us to decide when to discontinue larval theray? J Wound Care. Jan. 2004;13(1):38-40.

Steenvoorde P, Jukema GN. The antimicrobial activity of maggots: in-vivo results. J Tissue Viability. Jul. 2004 ;14(3):97-101.

Steenvoorde P, Oskam J. Bleeding complications in patients treated with maggot debridement therapy. Int J Low Extrem Wounds. Mar. 2005;4(1):57-8.

Steenvoorde P, van Doorn LP, Jacobi CE, Oskam J. Maggot debridement therapy in the pallative setting. Am J Hosp Palliat Care. Aug.-Sep. 2007;24(4):308-10.

Steenvorde et al., "Determining pain levels in patients treated with maggot debridement therapy," Journal of Wound Care, pp. 485-488, vol. 14, No. 10 Nov. 2005.

Steenvorde et al., "Maggot Debridement Therapy" Free-Range or Contained? an In-vivo Study, Advances in Skin and Wound Care, pp. 430-435, Oct. 2005.

Stevens et al., "Genetic Relationships between Bowflies (Calliphoridae) of forensic importance," Forensic Science International, 120 (2001) 116-123.

Stoddard et al., "Maggot Debridement Therapy, An Alternative Treatement for Nonhealing Ulcers," Selected papers from VA Hospitals and Medical Centers., Journal od the American Podiatric Medical Association. vol. 85, No. 4, Apr. 4, 1995, p. 218-221.

Summer JB, Kaminski J."Maggot debridement therapy for diabetic necrotic foot." Am Fam Physician Dec. 15, 2003;68(12):2327, 2330; author reply 2330.

Summers et al., "Letter to the Editor" Burns; 29, (2003) 501-502.

Tachibana et al., "Effects of Temperature and photoperiod on the termination of larva diapause in Lucilia sericata (Diptera: Calliphoridae)" Zoological Science 21:197-202 (2004).

Tantawi et al., "Clinical and microbiological efficacy of MDT in the treatment of diaetic foot ulcers," Journal of Wound Care, vol. 15, No. 9, Oct. 2007, pp. 379-383.

Tantawi et al., "Clinical and microbiological sutdies on the use of medicinal maggots in the management of diabetic foot ulcers," Abstract and poster from the 6th International Congress of Dipterology, Sep. 23-28, 2006, Fukuoka Japan.

Tech et al., "Maggot Therapy for severe skin infections," Maggot Therapy for Infected Wounds, Sep. 1986, 1153-1156.

Thomas "Cost of managing chronic wounds in the UK, with particular emphasis on maggot debridement therapy," Journal of Wound Care, vol. 15, No. 10, Nov. 2006, pp. 137-139.

Thomas et al., "The effect of containment on the properties of sterile maggots," British Journal of Nursing, 2002, vol. 11, No. 12.

Thomas S, Asaad SS. Vacuums and maggots in orthopaedic surgery. BMJ. May 13, 2006;332(7550):1156.

Thomas S, Jones M, Wynn K, Fowler T. The current status of maggot therapy in wound healing. Br J Nurs. Dec. 2001;10(22 Suppl):S5-8, S10, S12.

Thomas S, Jones M. Wound debridement: evaluating the costs. Nurs Stand. Feb. 14-20, 2001;15(22):59-61.

Thomas S., "The use of sterile maggots in wound management." Nurs Times. Sep. 3, 2002; 98(36):45-6.

Thomas, "The anti-microbial activity of maggot secretions: results of a preliminary study." J Tissue Viability. Oct. 1999;9(4):127-132.

Timmons et al., "The use of the versatile I wound vacuum system to treat a patient with a challenging grade 3 pressure ulcer in continuing care," Wounds UK, vol. 2, No. 2, pp. 125.

Townley WA, Jain A, Healy C. Maggot debridement therapy to avoid prosthesis removal in an infected total knee arthroplasty. J Wound Care. Feb. 2006;15(2):78-9.

van der Plas Mariena JA, Jukema GN, Wai S-W, Dogterom-Ballering HCM, Lagendjk EL, van Gulpen C, van Dissell JT, Bloem berg GV, Nibbering PH. Maggot excretions/secretions are differentially effective against biofilms of *Staphylococcus aureus* and *Pseudomonas aeruginosa*. Journal of Antimicrobial Chemotherapy. 2008;61:117-122.

Vaughan, Don, "Maggots, leeches and parasitic worms: These creepy critters might well make you shudder—but they might save your life," Weird Science, Military Officer, Aug. 2007, pp. 64-67.

Vistnes LM, Lee R, Ksander GA. Proteolytic activity of blowfly larvae secretions in experimental burns. Surgery. Nov. 1981;90(5):835-41.

Wainwright M. When maggot fumes cured tuberculosis. Microbiologist. Mar. 2007, pp. 33-35.

Wainwright, Milton, "Maggot Therapy—A Backwater in the fight Against Bacterial Infection," Pharmacy in History, vol. 30, (1998) No. 1, pp. 19-26.

Wang et al., "Treatment of Infected wounds with maggot therapy after replantation," Journal of Reconstructive Microsurgery, vol. 22, No. 4, 2006, pp. 277-279.

Wayman et al., "The cost effectiveness of larval therapy in venous ulcers," Journal of Tissue Viability, 2000 vol. 10, No. 3, pp. 91-94.

Wedi et al., "Biosurgical wound conditioning using maggot therapy and vacuum dressings following partial necrosis of a myocutaneous flap in the head and neck region following irradiation to this region," Mund Kiefer GesichtsChir 6, (2002), 437-441.

Wegner, Jennifer, "Medieval Mirical Workers, Are Maggots Making a Medical Comeback?" Jul. 20, 2004.

Whitaker et al., "Larval therapy from antiquity to th present day: mechanisms of action, clinical applications and future potential," Postgrad. Med. J. 2007, 83:409-413.

Whitaker IS, Welck M, whitiaker MJ, Conroy FJ. From the bible to biosurgery: *Lucilia sericata*—plastic surgeon's assisstant in the 21st century. Plast Reconstr Surg. Apr. 15, 2006;117(5):1670-1671.

Williams, Kirstin, "Maggot Debridement Therapy (MDT)" Palmut Post, vol. 9, No. 2, Dec. 2006, pp. 8-11.

Williamson, Elizabeth, "Maggot treatment makes skin crawl for some, Insect leaves healthy skin alone, eats dead flesh," Las Vegas Review Journal, Sunday, Sep. 28, 2003, p. 14A.

Wolff et al., Rearing Larva of *Lucilia sericata* for Chronic Ulcer Treatment—an Improved Method Acta Derm Venereol 2005; 85: 126-131.

Wolff H, Hansson C. Larval therapy—an effective method of ulcer debridement. Clin Exp Dermatol. Mar. 2003;28(2):134-7.

Wolff H, Hansson C. Larval therapy for a leg ulcer with methicillin-resistant *Staphylococcus aureus*. Acta Derm Venereol. Jul. 1999;79(4):320-1.

Wollina et al., "Biosurgery supports granulation and debridement in chronic wounds—clinical data and remittance spectroscopy measurement," International Journal of Dermatology, 2002, 41, 635-639.

Wollina et al., "Maggot therapy in the treatment of wounds of exposed knee prosthesis," Correspondence in International Journal of Dermatology 2005, 44, 884-886.

Yesko, Jill, "A Prescription for Maggots" Sky Magazine, Jun. 2006.

Zutt et al., "Successful Use of Vacuum-Assisted Closure Therapy for Leg Ulcers Caused by Occluding Vasculopathy and Inflammatory Vascular Diseases—A Case Series," Dermatology 2007; 214:319-324.

\* cited by examiner

MAGGOT DEBRIDEMENT THERAPY DRESSINGS AND METHODS

RELATED APPLICATIONS

This application claims priority under 35 U.S.C. section 119(e) from U.S. provisional application Ser. No. 61/079,087 filed Jul. 8, 2008, by Ronald Sherman, titled Maggot Debridement Therapy Dressings and Methods, which is incorporated by reference herein in its entirety.

FIELD OF THE INVENTION

Medical maggot therapy dressing embodiments and methods are discussed for the treatment of a variety of indications including wound care, including septic wound care and the like.

BACKGROUND

For centuries, the infestation of wounds by certain species of fly larvae or maggots has been recognized to debride, to enhance healing, and to decrease the mortality associated with the underlying injury. The practice of using maggots to treat bone and soft tissue infections was employed commonly by surgeons in North America during the 1930s and 1940s. The past 20 years have seen resurgence in the successful use of maggot debridement therapy for treating such afflictions as pressure ulcers, venous stasis ulcers, temporal mastoiditis, Fournier's gangrene, necrotizing tumor masses, and other soft tissue wounds that have not responded favorably to more conventional modalities.

The maggot debridement therapy dressings of 60 years ago were quite elaborate, expensive, and time-consuming to construct. Maggot debridement therapy dressings often consisted of either a maggot-filled cloth bag with its edges plastered to the wound margins or else an elaborate copper-mesh cage taped to the skin. Glass tubing sometimes was placed into a deep sinus in order to facilitate drainage and to prevent the top of the hole from closing prematurely.

During the 1970s and 1980s, a common maggot debridement therapy dressing included a simple gauze wrap over the maggot-laden wound. The nature of maggots, though, is that they will wander at will, and they will leave a wound once it is no longer nourishing or no longer necrotic. The maggots also will leave their food source when they are fully mature and attempt to seek an appropriate location for the pupation process which is the next stage in their metamorphosis into an adult fly. Gauze will not provide a sufficient barrier to their escape in any of these situations.

What has been needed are dressings for maggot debridement therapy that are inexpensive and convenient to apply. What has also been needed are dressings that are simple to maintain, durable enough to last throughout a therapeutic application period. What has also been needed are dressings that make the application of maggots and the confinement of maggots to a patient's wound site convenient and reliable.

SUMMARY

Some embodiments of a dressing for applying maggot debridement therapy to a patient's wound may include a flexible base layer having a contact surface suitable for skin contact and configured to releasably adhere in sealed relation to a patient's skin. The dressing may also include a flexible cover layer which is displaceable relative to the base layer and which has a mesh portion which includes a plurality of apertures configured to prevent passage of juvenile maggots, allow circulation of oxygen and allow wound drainage therethrough. An adhesive layer may be disposed between a bottom surface of the cover layer and a top surface of the base layer. The adhesive layer may be configured to adhere the bottom surface and top surface together in a sealed junction.

Some embodiments of a dressing for applying maggot debridement therapy to a patient's wound may include a flexible base layer having a contact surface suitable for skin contact and configured to releasably adhere to a patient's skin and a removable film disposed over the contact surface of the base layer. The dressing may also include a flexible cover layer which is secured to the base layer along an edge of the cover layer forming a hinged portion that allows the cover layer to be displaceable relative to the base in a hinged configuration. The cover layer may have a mesh portion which includes a plurality of apertures configured to prevent passage of juvenile maggots, allow circulation of oxygen and allow wound drainage therethrough. An adhesive layer may be disposed on a bottom surface of the cover layer. The adhesive layer may be configured to adhere the bottom surface and top surface when the surfaces are pressed together to form a sealed junction. A removable film may be disposed over the adhesive layer on the bottom surface of the cover layer to prevent exposure of the adhesive layer prior to use.

Some embodiments of a dressing for applying maggot debridement therapy to a patient's wound may include a flexible base layer having a contact surface suitable for skin contact and configured to releasably adhere to a patient's skin. The dressing may also include a flexible inner cover layer which is displaceable relative to the base layer and which has a mesh portion which includes a plurality of apertures configured to prevent passage of juvenile maggots, allow circulation of oxygen and allow wound drainage therethrough. An inner adhesive layer may be disposed between a bottom surface of the inner cover layer and a top surface of the base layer. The inner adhesive layer may be configured to adhere the bottom surface and top surface when the surfaces are pressed together to form a sealed junction. The dressing may also include a flexible outer cover layer which is displaceable relative to the inner cover layer and which has a mesh portion. An outer adhesive layer may be disposed between a bottom surface of the outer cover layer and a top surface of the inner cover layer. The outer adhesive layer may be configured to adhere the bottom surface of the outer cover layer and top surface of the inner cover layer when the cover layers are pressed together in a sealed junction.

Some embodiments of a method of maggot debridement therapy include removing an interior section of a flexible base layer of a maggot debridement therapy dressing to create an aperture in the base layer having a profile substantially corresponding to a profile of a patient's wound perimeter. A bottom surface of the flexible base layer may then be secured to the patient's tissue with the profile of the aperture of the base layer substantially aligned with the profile of the patient's wound perimeter. The base layer may be secured with an adhesive layer disposed between and in contact with the bottom surface and the patient's tissue. At least one maggot may then be applied to the patient's wound. A cover film is then removed from an adhesive layer disposed between the base layer and a cover layer to expose the adhesive layer and the cover layer is then secured to the base layer by pressing the base layer and cover layer together with the adhesive layer disposed therebetween.

These features of embodiments will become more apparent from the following detailed description when taken in conjunction with the accompanying exemplary drawings.

DETAILED DESCRIPTION

As discussed above, maggot debridement therapy is known to be an effective method of treatment of difficult non-healing wounds for many patients. Indications may include diabetic foot ulcers, bed sores, wounds resulting from spinal injuries and resulting immobility, leg ulcers, venus stasis wounds, non-healing post surgical wounds as well as any other appropriate difficult to heal wounds. Some problems commonly encountered when applying maggot debridement therapy may include keeping the maggots in the wound while placing the initial dressing, preventing the maggots from escaping through the dressings during the course of therapy, and preventing the dressing from being removed prematurely or accidentally by the nursing staff or other users of a dressing.

For some treatment embodiments, it may also be important for the maggots to have direct access to a patient's wound without a mesh or barrier layer disposed between the maggots and the necrotic tissue of the patient's wound. In addition, it may also be important to minimize contact of maggots with healthy non-necrotic skin of the patient. This may be useful in order to minimize an annoying sensory stimulation experienced by some patients from maggot contact with healthy innervated skin or other tissue. Other attributes that may be desirable for some embodiments include low cost, easy and controllable application and sufficient durability to maintain the above performance characteristics during a course of treatment of some acceptable subset of the course of treatment.

To meet one or more of these characteristics, some dressing embodiments include a base layer of material that is flexible enough to conform to irregular contours of a patient's skin. The base layer may also be sufficiently transparent or translucent in order to see or otherwise visualize a profile of a patient's wound through the base layer. Such visualization of the actual wound may be used to create an aperture in the base layer that has a profile that substantially conforms to the perimeter profile of the patient's wound. Predetermined wound profiles may also be marked or printed on the base layer during manufacture or prior to use to provide a user with reference points or lines for cutting an aperture in the base layer. For some embodiments, sets of progressive contour marks may be made on the base layer that provide outlines of apertures of varying size nested within each other. For some embodiments, the predetermined profile markings may be substantially round, elliptical, square, triangular or any other suitable shape in order to best conform to a patient's wound profile.

Referring to FIGS. 1-6, an embodiment of a dressing 10 for maggot debridement therapy is shown that may be applied to a patient's skin for the application of maggots to the patient's wound for cleaning, debriding and otherwise treating the patient's wound. The dressing 10 includes a flexible base layer 12 having a contact surface 14 suitable for skin contact and configured to releasably adhere to a patient's skin. A removable film 16 sometimes referred to as a protective liner is disposed over the contact surface 14 of the base layer 12 in order to protect the contact surface 14 from contamination or adhering to other surfaces or materials prior to use. The removable film 16 may be configured to extend laterally beyond the edges of the contact surface 14 of the base layer 12 in order to provide a tab portion that allows a user to more easily separate the protective film 16 from the contact surface 14.

Figure 1:
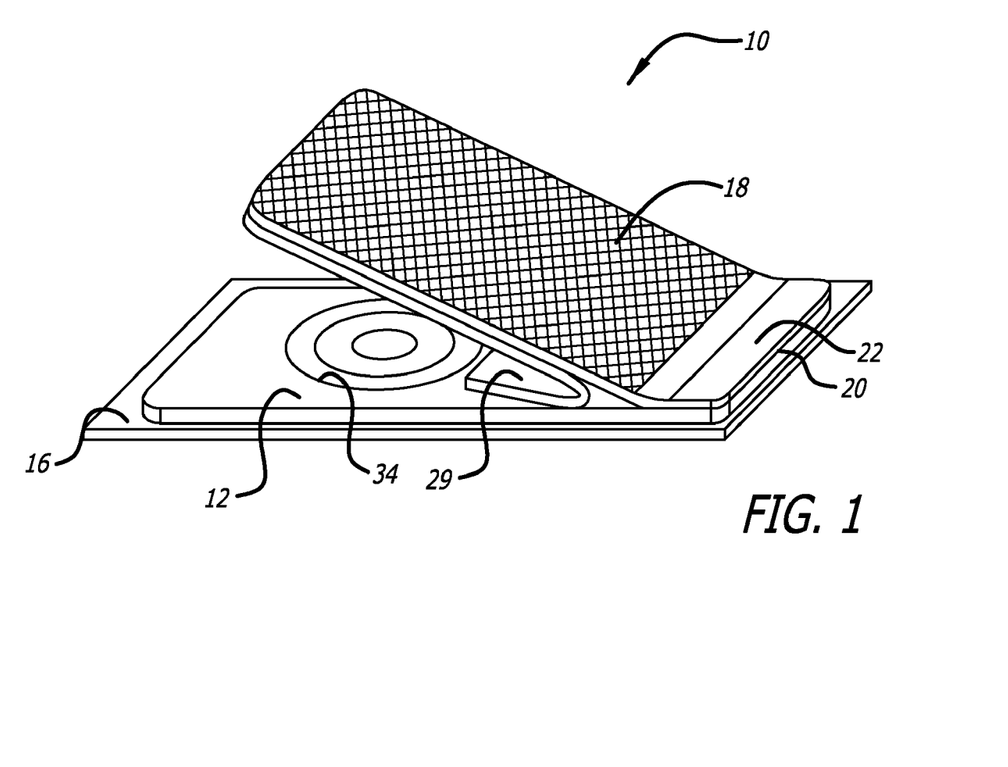
FIG. 1 is a perspective view of an embodiment of a dressing for maggot debridement therapy.
Figure 2:
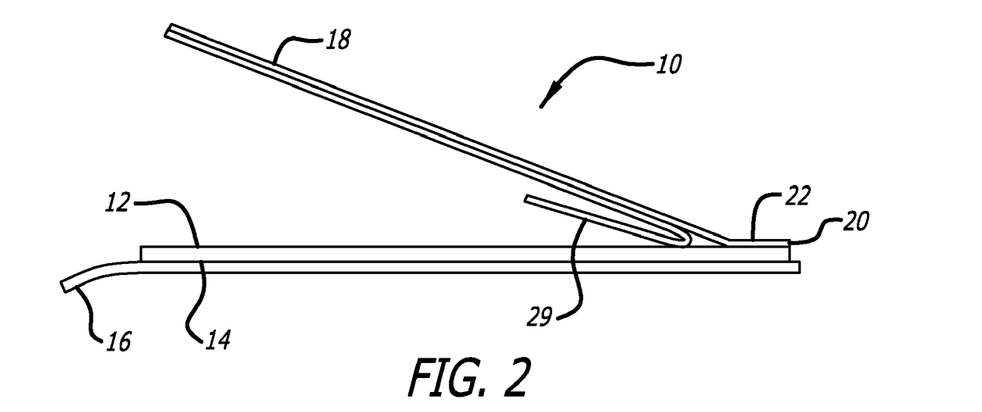
FIG. 2 is an elevation view of the dressing embodiment for maggot debridement therapy of FIG. 1.
Figure 3:
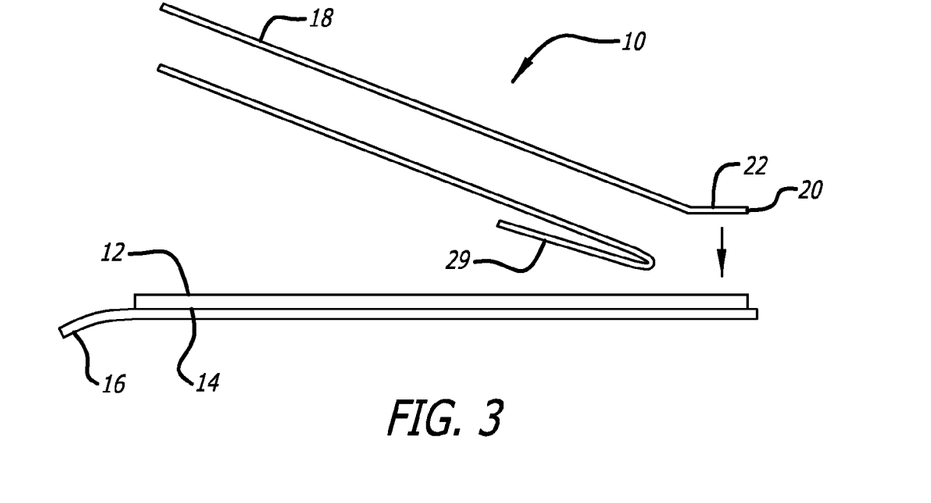
FIG. 3 is an enlarged exploded view of the dressing embodiment for maggot debridement therapy of FIG. 1.

A flexible cover layer 18 is secured to the base layer 12 along an edge 20 of the cover layer forming a hinged portion 22 that allows the cover layer 18 to be displaceable relative to the base layer 12 in a hinged configuration. The hinged portion 22 is disposed along the edge 20 of the cover layer 18 and a corresponding edge of the base layer 12 such that the cover layer 18 and base layer 12 will be substantially aligned with each other when the cover layer 18 is in a closed position in contact with the base layer 12. For some embodiments, the hinged portion 22 may be about 0.1 inch to about 0.5 inch wide and have a length that extends substantially along an entire side of both the cover layer 18 and base layer 12. The cover layer 18 has a mesh portion 24 which includes a plurality of apertures configured to prevent passage of juvenile maggots, allow circulation of oxygen and allow wound drainage therethrough. For the embodiment shown, the entire cover layer 18 includes a mesh portion 24.

Figure 4:
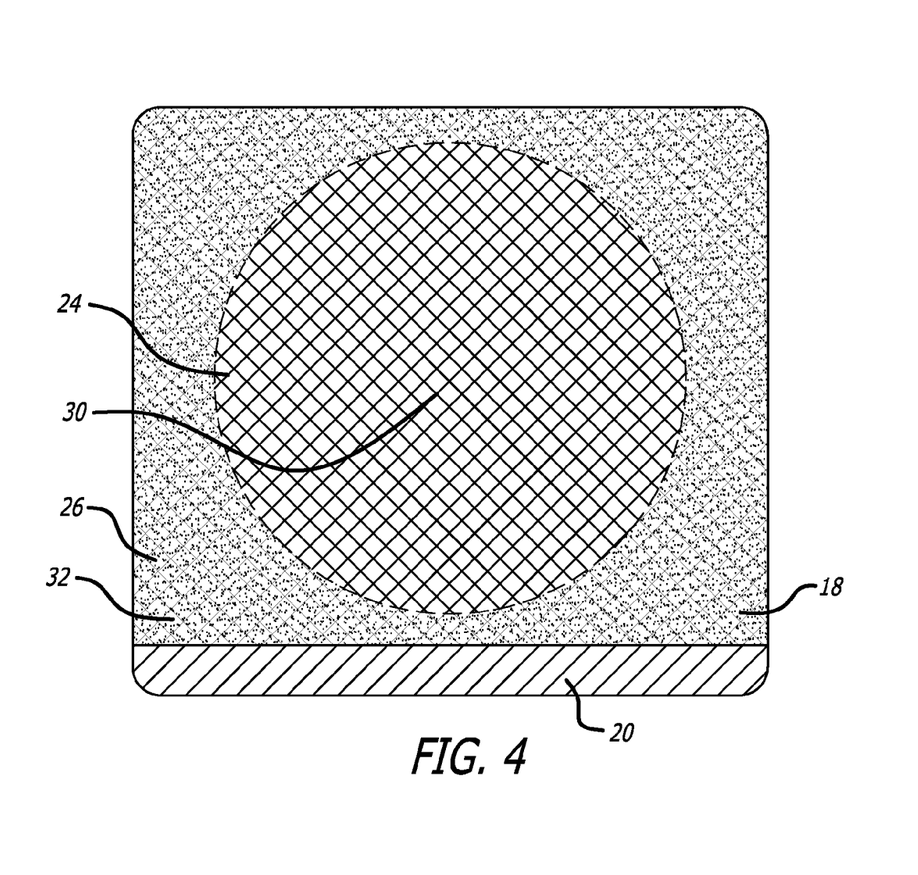
FIG. 4 is a bottom view of a flexible cover layer of the dressing embodiment for maggot debridement therapy of FIG. 1.

An adhesive layer 26, shown in FIG. 4, is disposed between a bottom surface of the cover layer 18 and a top surface of the base layer 12. For the embodiment shown, the adhesive layer 26 is disposed on the bottom surface of the cover layer 18 and is configured to adhere the bottom surface of the cover layer 18 and a top surface of the base layer 12 together in a sealed junction. For some embodiments, the hinged portion 22 may be formed by partial adhesion of the adhesive layer 26 to the base layer 12. The adhesive layer 26 may be very thin and include a surface application of adhesive material to the bottom surface of the cover layer 18 or top surface of the base layer 12 in some embodiments and need not form a layer in the dressing of appreciable thickness.

Figure 13:
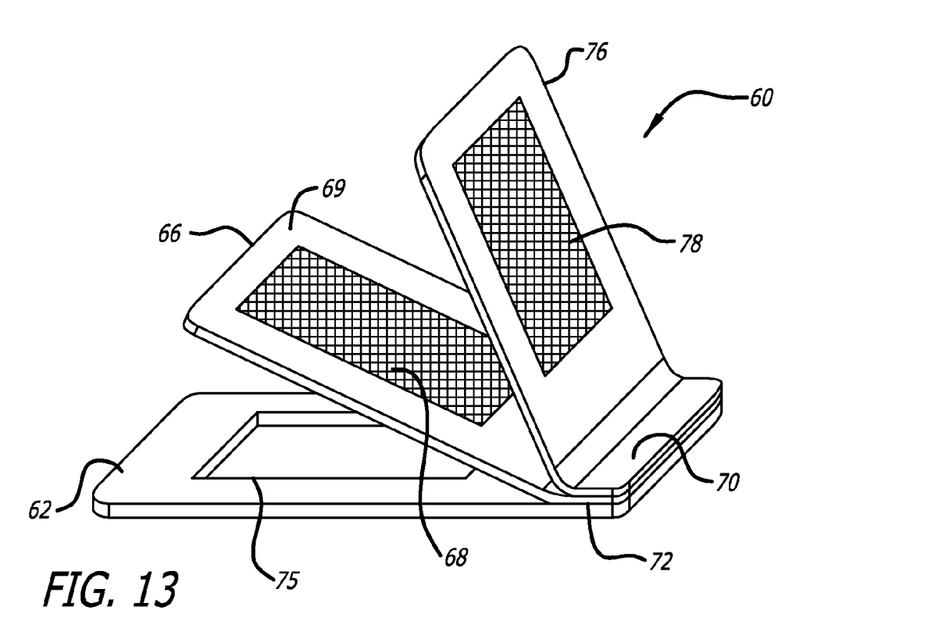
FIG. 13 is a perspective view of a dressing for maggot debridement therapy having a base layer, an inner cover layer and an outer cover layer.
Figure 14:
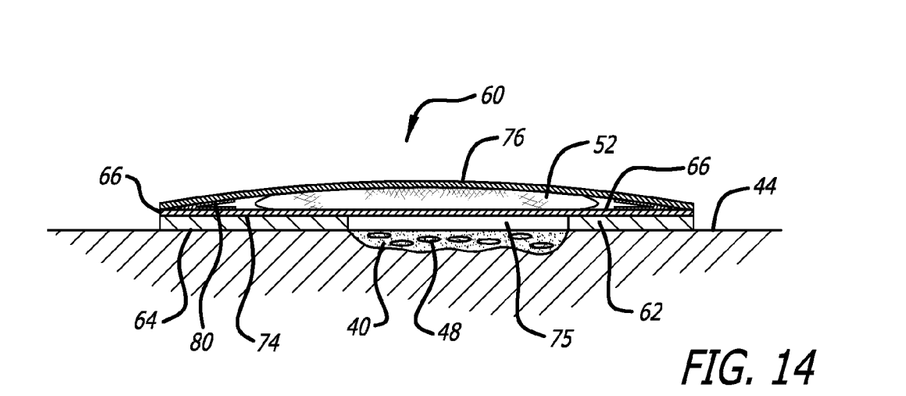
FIG. 14 is an elevation view of the dressing of FIG. 13 deployed on a patient's wound with absorbent material disposed between the mesh portion of the inner cover layer and a mesh portion of the outer cover layer.

The cover layer 18 may have substantially the same transverse size and shape as the transverse size and shape of the base layer 12 and such a cover layer 18 may be configured to cover an outline of the base layer 12. The cover layer 18 may also be somewhat larger or somewhat smaller than the base layer 12 for some embodiments. Although the cover layer embodiment 18 shown includes a mesh portion over the entire span of the cover layer, it may also be constructed with a frame portion that encompasses a mesh portion disposed within the frame portion as shown in the embodiment of FIGS. 13 and 14 discussed below. For such embodiments, the cover layer may include a perimeter or frame portion of flexible material, such as hydrocolloid, and an interior mesh portion of a mesh having a plurality of apertures that are configured to prevent passage or egress of juvenile maggots, such as juvenile blow fly maggots, allow passage and circulation of oxygen and allow drainage of necrotic tissue and maggot waste from the wound. The mesh portion and frame portion of such cover layer embodiments may generally lie in a planar configuration with the mesh portion and frame portion lying in substantially the same plane. The mesh portion 24 of cover layer embodiment 18 shown in FIGS. 1-6 may also lie substantially in a plane when in a relaxed, non-deformed state. For some embodiments, the base layer, cover layer or layers or all of these may be flexible enough to conform to an irregular surface of a patient's skin adjacent to a wound site yet sufficiently resilient to maintain its general shape during manipulation by a user during application.

The mesh portion 24 of the cover layer may include any suitable configuration of a layer having appropriately sized apertures and a sufficient number of the apertures to provide a desired performance. Some mesh portion embodiments 24 may include perforated layers, spun fiber layers, woven or braided fiber layers or the like and may be made from any suitable natural or synthetic material or materials such as cotton, silk, polyester or the like. For some embodiments, the mesh portion 24 of the cover layer 18 may include a polyester based mesh or chiffon material such as Petex® fabric manufactured by Sefar company headquartered in Heiden, Switzerland. The apertures of the mesh portion 24 may be large enough to allow sufficient wound drainage and air circulation of the wound and small enough to prevent the escape or egress of juvenile maggots confined by the mesh portion in a patient's wound. For some embodiments, the apertures of the mesh portion 24 may have a maximum size or transverse dimension of about 25 microns to about 250 microns, more specifically, about 100 microns to about 200 microns, and even more specifically, about 140 microns to about 160 microns. For some embodiments, the mesh portion 24 may have a thickness of about 0.001 inches to about 0.25 inches. The porosity of the mesh portion 24 may vary depending on the indication, total surface area of the mesh, number of maggots contained as well as other factors. For some embodiments, the mesh portion may have a porosity of about 25 percent to about 70 percent total pore or aperture area per unit area of mesh fabric.

Some mesh portion materials and construction techniques may produce apertures that are substantially non-expandable. The Petex® material discussed above may be such a material. However, some other mesh portion embodiments 24 may include materials and construction, such as nylon stocking material or the like, that allow the apertures in the mesh portion 24 to elastically expand in a limited fashion to a predetermined maximum aperture size or transverse dimension. For such embodiments, it may be desirable for the maximum aperture size to be commensurate with the maximum aperture size suitable for preventing escape of juvenile maggots. For example, the predetermined maximum aperture size for some expandable mesh portion embodiments 24 may be about 25 microns to about 250 microns, more specifically, about 100 microns to about 200 microns, and even more specifically, about 140 microns to about 160 microns.

For some embodiments, the adhesive layer 26 may be made from an adhesive material that is re-securable. A re-securable material may be separated from a surface and then re-secured to the surface or another surface if desired. This re-securable adhesive material may allow a use to secure and seal the cover layer 18 to the base layer 12, separate the cover layer 18 from the base layer 12 in order to access a patient's wound, and then re-secure the cover layer 18 to the base layer 12. For some embodiments, this process may be repeated multiple times. A removable film 28 is disposed over a contact surface of the cover layer 18 in order to protect a contact surface 30 of the adhesive layer 26 from contamination or adhering to other surfaces or materials prior to use. The removable film may include a tab portion 29 extending from the cover layer 18 that is loose and exposed and provides an accessible tab for a user to grasp and pull in order to more easily remove the removable layer 28.

The adhesive layer 26 may be disposed on all of the cover layer 18 or only a desired portion thereof. For example, the adhesive layer 26 may be disposed only on the portions of the cover layer 18 that will be in contact with the base layer 12 after the base layer 12 has an aperture formed therein, particularly in embodiments where the aperture in the base layer 12 will have a known profile and size. In addition, the adhesive layer 26 may be applied to a perimeter of the cover layer 18 with a relatively large area within the perimeter that is free of adhesive layer 26. FIG. 4 illustrates a bottom view of a cover layer embodiment 18 showing a substantially circular non-adhesive section 30 in a middle portion of the cover layer 18 and a perimeter portion 32 having an adhesive layer 26 disposed thereon. The cover layer 18 is shown without the removable film 28 for purposes of illustration. This configuration allows the perimeter of the cover layer 18 to adhere to the base layer 12 around its perimeter without exposing the maggots deployed in the patient's wound to a sticky surface of the adhesive layer 26.

The adhesives used for the contact surface of the base layer 12 and the adhesive layer 26 disposed between the base layer 12 and cover layer 18 may be configured to withstand ongoing exposure to materials such as necrotic tissue drainage, maggot waste and the like. For some embodiments, the adhesive material or materials used for the dressing 10 may be configured to maintain their adhesive properties when exposed to such materials and may be re-sealable for some applications. For some embodiments, the adhesive materials may include film adhesives, gels, or pastes. For some embodiments, the adhesive layer may include a rubber base material such as part number HT-513793 manufactured by Hi-Tech Products, Buena Park, Calif.

In order to facilitate sizing of an aperture to be created in the base layer 12 that may have a profile that conforms to a perimeter profile of a patient's wound, it may be desirable for the base layer 12 to be sufficiently transparent or translucent to view an outline of a patient's wound through the base layer 12. In this way, the base layer 12 may be placed adjacent the patient's wound with the removable film 16 over the contact surface 14 such that the contact surface 14 does not adhere to the patient's skin around or on the wound. A user may use the transparency or translucent character of the base layer 12 to visualize an outline of the wound perimeter profile through the base layer 12 due to the color or shading distinction between the wound and the healthy skin adjacent the wound. The user may then mark an approximation of the wound perimeter profile directly on the base layer 12 with a marking pen or the like and cut out an aperture in the base layer 12 according to the marked perimeter. The user may also use an iterative process wherein the base layer 12 is disposed adjacent the wound and the wound perimeter profile visualized and an aperture approximating the profile of the wound cut into the base layer 12 without the marking process. The base layer 12 may then be disposed adjacent the wound again and the profile of the aperture checked against the profile of the wound. Thereafter, additional material may be removed from the base layer 12 where necessary and the process continued until a desired fit has been achieved.

Figure 5:
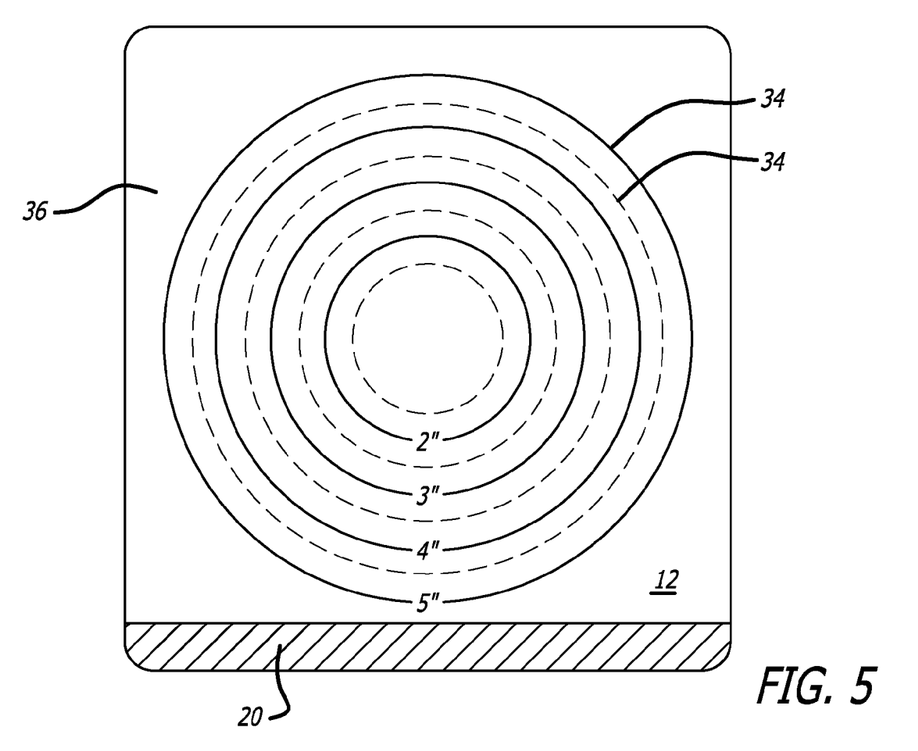
FIG. 5 is a top view of a base layer of the dressing embodiment for maggot debridement therapy of FIG. 1.
Figure 6:
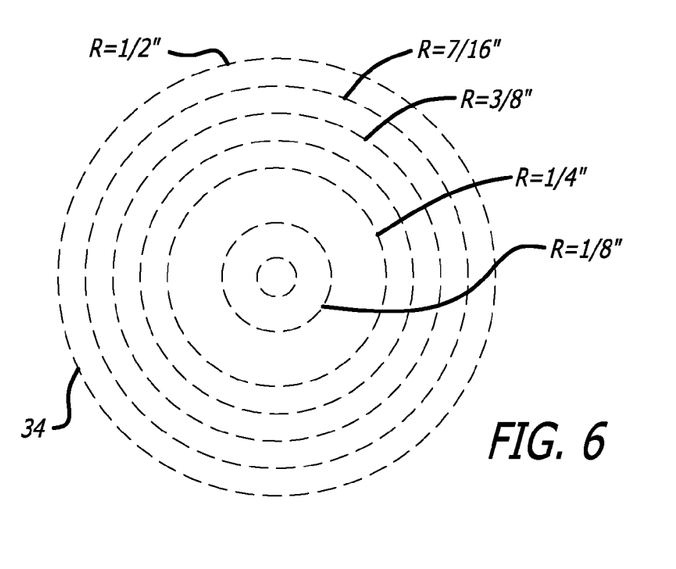
FIG. 6 is a schematic view of concentric profile outline embodiments for marking a base layer of a dressing maggot debridement therapy.

For some embodiments, the base layer 12 may include pre-applied visible markings 34 on either surface which may be configured to provide an outline for cutting an aperture in the base layer 12 to substantially encompass a patient's wound perimeter. The pre-applied markings 34 may have any suitable predetermined shape or configuration and may be disposed in concentric or progressively larger profiles. The user may then choose a particular marking profile and cut the base layer 12 accordingly for the desired fit of the aperture cut into the base layer 12 relative to the patient's wound perimeter profile. FIG. 5 illustrates a top view of a base layer 12 embodiment having pre-applied markings 34 on a top surface 36 of the base layer 12 that are formed in concentric rings with alternating solid and dashed lines. The pre-applied markings 34 are disposed in increments of about a 1.5 inch diameter, a 2 inch diameter, a 2.5 inch diameter, a 3 inch diameter, a 3.5 inch diameter, a 4 inch diameter, a 4.5 inch diameter and a 5 inch diameter, although any suitable desired size or profile shape may be used. For example, pre-applied markings 34 may be used having substantially square, round, elliptical, or triangular profiles or any other suitable shape. FIG. 6 shows concentric dashed lines representing pre-applied markings for a base layer embodiment disposed in increments of about ½ inch, 7/16 inch, ⅜ inch, ¼ inch and ⅛ inch.

For some embodiments, a similar series of concentric apertures (for example, circular or quadrangular) may be partially cut or perforated through the base layer 12 without being removed at the time of manufacture. In the latter case, the material corresponding to the profile that best matches the wound profile may be removed along the corresponding perforation by the user. For some embodiments, the base layer 12 may have an aperture already cut out during manufacture to approximate the dimensions of the wound. For example, such a dressing configuration might be produced with base layers 12 that come in a variety of sizes and configurations to match corresponding wound sizes and configuration. Some pre-manufactured base layer apertures may include circular, square, or other shaped holes in the base layer thereof with the holes or apertures having a surface area of about 1 $cm^2$, 2 $cm^2$, 3 $cm^2$, or more. Any of the base layer embodiments discussed may have an aperture or apertures formed therein having an area of about 1 $cm^2$ to about 35 $cm^2$, more specifically, about 2 $cm^2$ to about 12 $cm^2$. Some base layer embodiments may have apertures formed therein having an area up to about 600 inches square or more.

For some embodiments, the base layer 12 may include a hypoallergenic material that is flexible enough to conform to a curved or irregular profile of a patient's skin or other tissue. For some embodiments, the base layer 12 may be flexible enough to conform to an irregular surface of a patient's skin adjacent a wound site yet sufficiently resilient to maintain its general shape during manipulation by a user during application or cutting of the wound aperture in the base layer 12. One suitable material for the base layer 12 includes hydrocolloid materials such as Duoderm® manufactured by Convatec, Inc. or similar materials manufactured by Hi-Tech Products, Buena Park, Calif. Other suitable materials for the base layer 12 may include hydrogels, silicones, foams, and the like. For some embodiments, the thickness of the base layer 12 may be about 0.001 inches to about 0.25 inches, more specifically, about 0.02 inches to about 0.1 inches. For some embodiments, the base layer 12 and cover layer 18 may each have an area of about 1 square inch to about 1000 square inches or more, more specifically, about 2 square inches to about 600 square inches, and even more specifically, about 5 square inches to about 150 square inches. For some substantially square embodiments of the dressing 10, the base layer 12 and cover layer 18 may have outer transverse dimensions of about 1 inch to about 2 inches. For some embodiments, the outer transverse dimension of the base layer 12 may be about 10 inches to about 14 inches. Some embodiments of the base and cover layers may have outer transverse dimensions of about 20 inches to about 28 inches.

Figure 7:
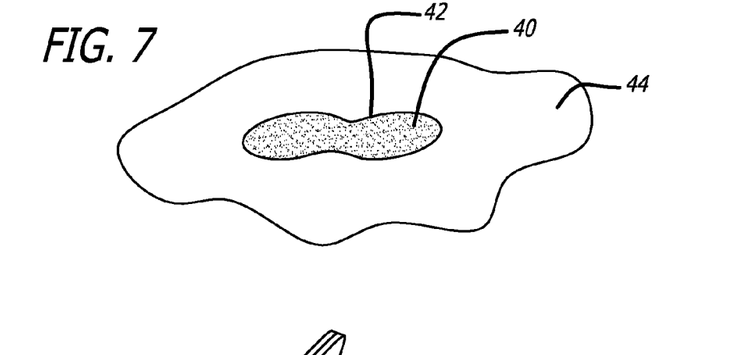
FIG. 7 is a perspective view of a patient's wound showing a profile of the patient's wound perimeter.

Referring to FIGS. 7-12, an embodiment of a method of applying maggot debridement therapy is illustrated. FIG. 7 shows a schematic view of a patient's wound 40 having an irregular perimeter profile 42 formed into a patient's skin 44 that has a relatively healthy condition adjacent the patient's wound 40. Such a wound 40 may include necrotic tissue that involves the patient's skin 44 and underlying tissue or tissues including fat, muscle, connective tissue and the like. Initially, an interior section of a flexible base layer 12 of a maggot debridement therapy dressing 10 may be removed to create an aperture 46 in the base layer 12 having a profile substantially corresponding to a profile 42 of a patient's wound perimeter.

For such a wound 40, a user may place a dressing for maggot debridement therapy, such as dressing 10, adjacent and over the wound 40 in order to approximate the perimeter profile 42 of the wound 40 and form an aperture 46 in the base layer 12 of the dressing 10 that has a profile that substantially matches the perimeter profile of the wound 40. For dressing embodiments having a transparent or translucent base layer, the base layer 12 may be disposed over the wound and the wound perimeter profile visualized through the material of the base layer. The wound perimeter profile may then be marked onto an upper surface of the base layer 12 and subsequently cut out. The wound perimeter profile may also be approximated visually and cut out without applying markings to outline the profile. For dressing embodiments that do not have a transparent or translucent base layer, the aperture 46 in base layer 12 may be approximated in an iterative process where a user cuts an aperture that is the user's best approximation to the profile of the wound perimeter, then holds the base layer 12 adjacent the wound 40 and notes where additional base layer material needs to be removed. Once the additional base layer material is removed, the base layer 12 is once again disposed adjacent the wound 40 and the profile of the aperture in the base layer 12 and the wound profile compared. The process may be repeated until the aperture 46 achieves a desired match to the wound.

Figure 8:
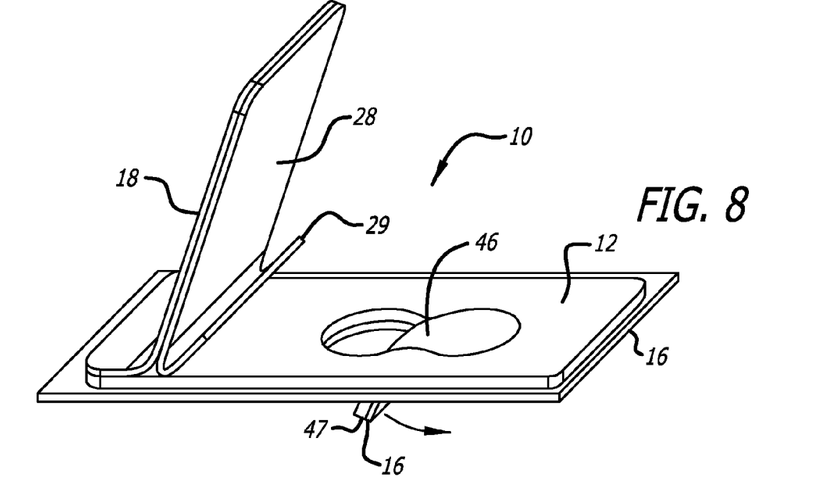
FIG. 8 is a perspective view of the dressing of FIG. 1 wherein a profile substantially matching the profile of a patient's wound perimeter of FIG. 7 has been formed into the base layer.

For embodiments which require the user to cut an aperture 46 in the base layer 12, the aperture 46 in the base layer 12 may be formed by any suitable method using any suitable tool or equipment. For some embodiments, the aperture 46 in the base layer 12 may be cut into the base layer 12 with scissors, or a sharp instrument such as a scalpel or Exacto® type blade. FIG. 8 shows the base layer material 47 being removed from the aperture 46 formed in the base layer 12 after the aperture profile has been cut into the base layer material with scissors. For some embodiments, an aperture 46 may already be cut out of the base layer 12 as discussed above. For some embodiments, a series of concentric apertures may be partially cut or perforated into the base layer material without being removed. In the latter case, the base layer material within the best-matching concentric aperture may be removed by the user in a manner similar to that shown in FIG. 8 where connective elements (not shown) of a perforation line are manually separated or severed.

Figure 9:
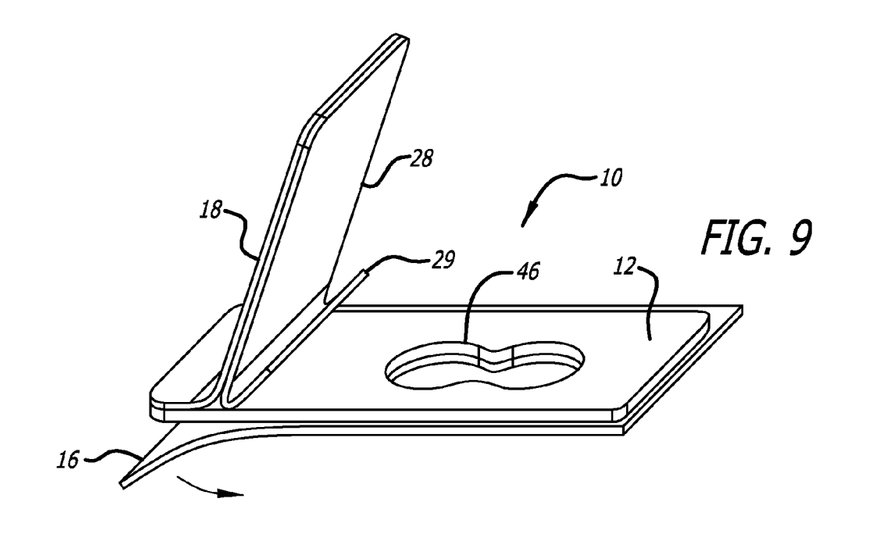
FIG. 9 is a perspective view of the dressing of FIG. 8 wherein a removable film is being peeled away from a contact surface of the base layer of the dressing.
Figure 10:
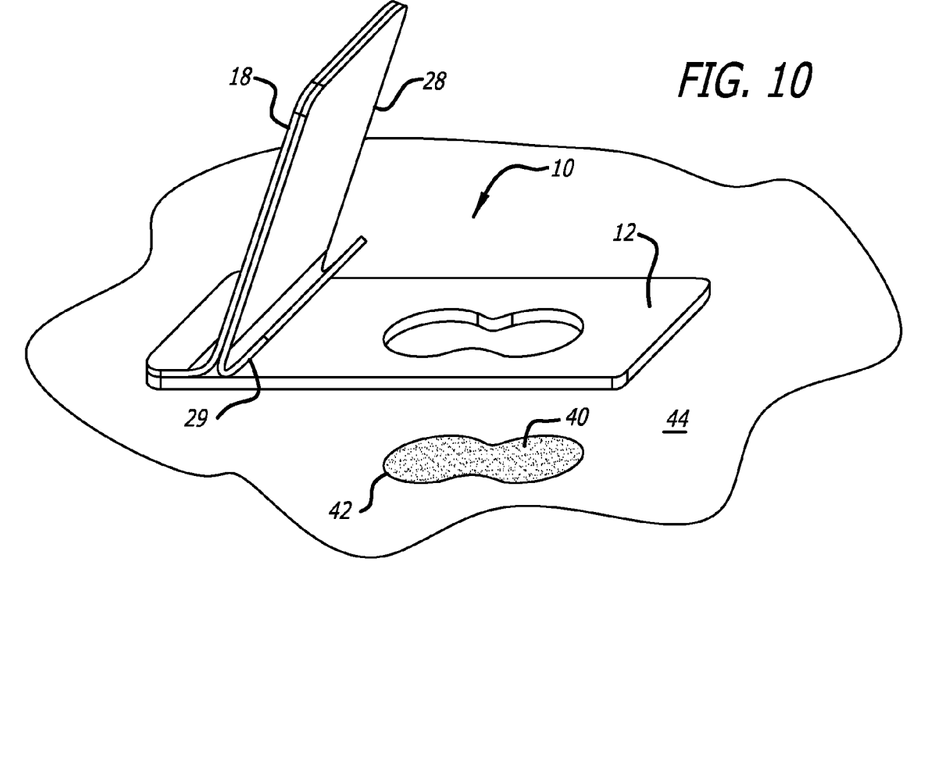
FIG. 10 is a perspective view of the dressing being applied to a patient's skin with the profile of the aperture in the base layer substantially aligned with the profile of the perimeter of the patient's wound.
Figure 11:
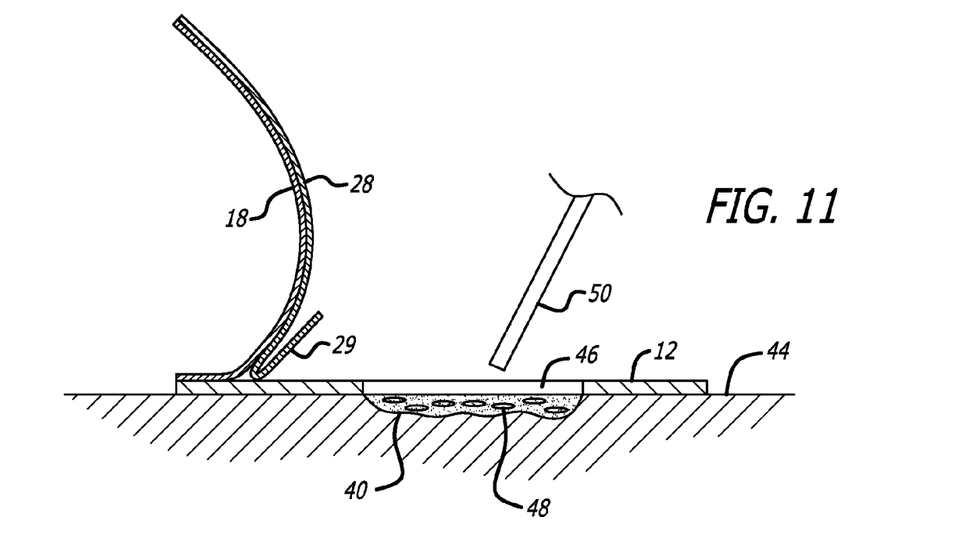
FIG. 11 is an elevation view in partial section illustrating the application of juvenile maggots to the patient's wound through the aperture in the base layer of the dressing.

Once an appropriately sized and configured aperture 46 has been made in the base layer 12 of the dressing 10, the protective removable film 16 covering the adhesive contact surface 14 of the base layer 12 may be removed as shown in FIG. 9. Removal of the film 16 exposes the adhesive material on the contact surface 14 that is configured to be releasably secured or adhered to the patient's skin 44. Next, the contact surface 14 of the flexible base layer 12 may be positioned adjacent the wound 40 as shown in FIG. 10. Once the base layer 12 of the dressing is positioned in a desired site, the contact surface of the base layer may then be secured by adhesion or other suitable means to the patient's tissue 44 with the profile of the aperture 46 of the base layer 12 substantially aligned with the profile of the patient's wound perimeter 42 as shown in FIG. 11. Once so deployed, the adhesive disposed on the contact surface 14 of the base layer 12 is disposed between and in contact with the bottom or contact surface 14 of the base layer 12 and the patient's tissue, such as the patient's skin 44, providing a releasable junction between these surfaces. A seal may also be formed between the patient's skin 44 adjacent the wound 40 and the contact surface 14 of the base layer 12.

Once the dressing 10 is deployed on the patient's skin 44, at least one maggot 48 may be applied through the aperture 46 in the base layer 12 and into or onto the patient's wound 40. FIG. 11 also shows a depiction of maggots 48 being applied to a patient's wound 40 through an elongate tubular member 50. The dosimetry of maggot application may vary greatly depending on the size and type of the patient's wound 40 as well as other factors. For some indications, approximately 5 maggots to about 10 maggots, such as blow fly maggots, may be applied for each square centimeter of wound area. For some treatment embodiments, it may also be desirable to apply maggots 48 at a particular age or stage of development. For some embodiments, maggots 48, such as blow fly maggots, may be applied to the patient's wound 40 at an age of about egg stage to about early $3^{rd}$ instar (relatively late in the maggots development), more specifically, about $1^{st}$ or $2^{nd}$ instar (early to mid-stage). The maggots 48 may be applied to the wound 40 through the aperture 46 in the base layer 12 by any suitable method such as pouring them out in an aqueous suspension, (for example, through a funnel), transferring them on a gauze pad or similar vehicle, or simply transferring the gauze or material on which they are located within a vial and placing that gauze or material on the wound 40. For some embodiments, suitable maggots for treatment of a patient's wound may include a safe and effective species and strain of maggot which may be germ-free as a result of disinfection, such as chemical disinfection. Some such effective maggots may include a pure strain such as the LB-01 strain of *Phaenicia* (*Lucilia*) *sericata*. Maggots such as these are discussed in "Maggot Therapy Takes Us Back to the Future of Wound Care: New and Improved Maggot Therapy for the 21 st Century", R. Sherman, *Journal of Diabetes Science and Technology*, Vol. 3, Issue 2, (March 2009), which is incorporated by reference herein in its entirety.

Figure 12:
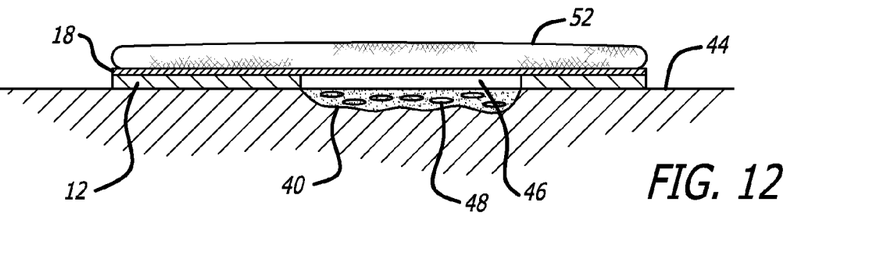
FIG. 12 is an elevation view in partial section of the dressing over the patient's wound with the maggots deployed within the wound and with a cover layer of the dressing sealed to the base layer.

Once a desired dose of maggots 48 have been applied to the patient's wound 40 through the aperture 46 in the base layer 12, the removable film or protective liner 28 may then be removed from the adhesive layer 26 which is disposed between the base layer 12 and a cover layer 18. The cover layer 18 may then be secured to the base layer 12 by pressing the base layer 12 and cover layer 18 together with the adhesive layer 26 disposed therebetween as shown in FIG. 12. For some embodiments, securing the cover layer 18 to the base layer 12 may include pivoting the cover layer 18 at the hinge portion 22 towards the base layer 12. For some embodiments, the adhesive layer 26 may be configured to be a re-sealable adhesive that may allow subsequent separation and re-sealing between the cover layer 18 and the base layer 12.

As discussed above, the cover layer 18 may include a mesh portion 24 having apertures that confine the maggots to the wound 40 and allow draining of the patient's wound 40 through the mesh portion 24 of the cover layer 18 and circulation of oxygenated air in the patient's wound 40 through the mesh portion 24 of the cover layer 18. The deployed dressing 10 shown in FIG. 12 has a continuous seal between the contact surface 14 of the base layer 12 and the patient's skin 44 around the patient's wound 40. At least a perimeter of the cover layer 18 is secured and sealed to a top surface of the base layer 12 and the mesh portion 24 of the cover layer 18 is sealed to or integral with the cover layer 18. As such, a substantially continuous seal may be formed between a perimeter of the patient's skin 44 disposed around the wound 40 and the mesh portion 24 of the dressing 10 which allows the wound 40 to drain, allows aeration of the wound and the deployed maggots 48 and allows potential visualization of the wound 40 through the mesh portion 24. For some treatment embodiments an absorbent material 52 may be applied over the mesh portion 24 of the cover layer 18 after deployment of the dressing 10. The absorbent material may include any suitable medical grade material such as gauze, sponges, foam or the like. The absorbent material may serve to soak up wound drainage fluids as well as other purposes.

For some embodiments of dressings for maggot debridement therapy, an outer or second cover layer having a mesh portion may be secured to the cover layer which is secured to the base layer. For such embodiments, an absorbent material 52 may be disposed between the mesh portion of the cover layer and a mesh portion of the outer cover layer as discussed with respect to the dressing embodiment 60 shown in FIGS. 13 and 14 and discussed below.

Referring to FIG. 13, an embodiment of a dressing 60 for maggot debridement therapy is shown that may have many features, dimensions and materials which are the same as, or similar to, the features, dimensions and materials of the dressing 10 for maggot debridement therapy shown in FIGS. 1-6 and discussed above. The dressing 60 includes a flexible base layer 62 having a contact surface 64 suitable for skin contact which is configured to releasably adhere to a patient's skin. A flexible inner cover layer 66 is displaceable relative to the base layer 62. The inner cover layer 66 includes a mesh portion 68 that lies in substantially the same plane as a perimeter or frame portion 69 of the inner cover layer. For some embodiments, the inner cover layer 66 may be secured to the base layer 62 along an edge 70 of the inner cover layer 66 forming a hinged portion 72 that allows the inner cover layer 66 to be displaceable relative to the base layer 62 in a hinged configuration. The hinged portion 72 is disposed along the edge 70 of the inner cover layer 66 and a corresponding edge of the base layer 62 such that the inner cover layer 66 and base layer 62 will be substantially aligned with each other when the inner cover layer 66 is in a closed position in contact with the base layer 62. For some embodiments, the hinged portion 72 may be about 0.1 inch to about 0.5 inch wide and have a length that extends substantially along an entire side of both the inner cover layer 66 and base layer 62.

The mesh portion 68 of the inner cover layer 66 includes a plurality of apertures configured to prevent passage of juvenile maggots, allow circulation of oxygen and allow wound drainage therethrough. An inner adhesive layer 74 may be disposed between a bottom surface of the inner cover layer 66 and a top surface of the base layer 62. The inner adhesive layer 74 is configured to adhere the bottom surface of the inner cover layer 66 and top surface of the base layer 62 together in a sealed junction. The inner adhesive layer 74 may be disposed in a perimeter portion of the surface of the inner cover layer 66 or base layer 62 in order to prevent adhesive placement in the mesh portion 68 and prevent exposure to contained maggots 48 or wound tissues to adhesive material.

The base layer 62 may include pre-marked profiles or perforations (not shown) or any other suitable features as discussed above with regard to base layer 12 to assist a user with creating an aperture 75 in the base layer 62 that matches a patient's wound profile as discussed above. For some embodiments, the thickness of the base layer 62 may be about 0.001 inches to about 0.25 inches, more specifically, about 0.02 inches to about 0.1 inches. For some embodiments, the base layer 62 and inner cover layer 66 may each have an area of about 1 square inch to about 1000 square inches or more, more specifically, about 2 square inches to about 600 square inches, and even more specifically, about 5 square inches to about 150 square inches. For some substantially square embodiments of the dressing 60, the base layer 62 and cover layer 66 may each have outer transverse dimensions of about 1 inch to about 2 inches square. For some embodiments, the base layer 62 and cover layer 66 may have outer transverse dimensions of about 10 inches to about 14 inches. Some embodiments of the base and cover layers may have an outer transverse dimension of about 20 inches to about 28 inches.

A flexible outer cover layer 76 which is displaceable relative to the inner cover layer 66 also has a mesh portion 78 that includes one or more apertures configured to be absorptive or to secure an absorptive material while still allowing the circulation of oxygen into the wound and allowing wound drainage into a top absorptive layer or material. The outer cover layer 76 may have a hinged configuration relative to the inner cover layer 66 and base layer 62 that is similar to or the same as the hinged configuration between the inner cover layer 66 and base layer 62. An outer adhesive layer 80 is disposed between a bottom surface of the outer cover layer 76 and a top surface of the inner cover layer 66. The outer adhesive layer 80 is configured to adhere the bottom surface of the outer cover layer 76 and top surface of the inner cover layer 66 to join the cover layers together in a sealed junction at a perimeter portion of the cover layers. The outer adhesive layer 80 may also include a resealable adhesive such as those adhesives discussed above. Examples of adhesives for the outer cover layer 76 may also include film adhesive, Velcro®, zippers, tape, ties or any other suitable material or method. The outer cover layer 76 may not need to be sealed to the inner cover layer for some embodiments when deployed, as the sealed structure that contains deployed maggots contained by the dressing 60 may be formed by the base layer 62 and inner cover layer 66.

Once a dressing 60 has been deployed with the base layer 62 secured to the patient's skin and the inner cover layer 66 secured to the base layer 62, an absorbent material 52 such as gauze, sponges or any other suitable and useful material may be disposed between the inner cover layer 66 and outer cover layer 76. The outer cover layer 76 may then be secured to the inner cover layer with the outer adhesive 80 which may be exposed by removal of a removable protective film (not shown) and the application of pressure between the inner cover layer 66 and outer cover layer 76. A cross section of a dressing 60 deployed over a patient's wound 40 is shown in FIG. 14 with the absorbent material 52 disposed between the mesh portions of the inner cover layer 66 and outer cover layer 76. For the embodiment 60 show in FIG. 14, a continuous seal exists between the contact surface of the base layer 62 and the patient's skin 44 around the patient's wound 40. At least a perimeter of the inner cover layer 66 is secured and sealed to a top surface of the base layer 62 and the mesh portion 68 of the inner cover layer 66 is sealed to or integral with the perimeter or frame portion 69 of the inner cover layer 66. As such, a substantially continuous seal is formed between a perimeter of the patient's skin 44 disposed around the wound 40 and the mesh portion 68 of the inner cover layer 66 of the dressing 60 which allows the wound to drain, aeration of the wound and deployed maggots 48 and potential visualization of the wound through the mesh portion 68.

The absorbent material 52 applied over the mesh portion 68 of the inner cover layer 66 is held in place by the outer cover layer 76 which is secured to the inner cover layer 66 by the outer adhesive layer 80. For the cover layer embodiments shown, the mesh portion is disposed within an interior portion of an outer perimeter portion that may serve to add additional structural integrity to the cover layer embodiments as well as adding thickness to the cover layer structure. For such cover layer embodiments, which may be used for embodiments such as those shown in FIG. 1 or 13, the perimeter portion or frame 69 of the cover layers may be made from a flexible hypoallergenic material such as hydrocolloid or the like. The thickness of the perimeter or frame 69 of the cover layer embodiments may be about 0.01 inch to about 0.25 inch, depending on the desired thickness. For some embodiments, a perimeter material that is thicker than the mesh portion material may be useful to produce a pocket or cavity between the adjacent mesh portions or between a mesh portion of the inner cover layer 66 and the patient's wound tissue.

For some embodiments, the entire inner cover layer 66 includes a mesh portion. For some embodiments, the inner cover layer 66 and outer cover layer 76 have substantially the same size and shape as the size and shape of the base layer 62. For such embodiments, the inner cover layer may be configured to cover an outline of the base layer 62. The mesh portions of the inner cover layer 66 and outer cover layer 76 may have the same features, dimensions and materials as those of the mesh portion of the cover layer 18 of the dressing 10 shown in FIG. 1 and discussed above. In addition, the base layer 62 may have the same features, dimensions and materials as those of the base layer 12 of the dressing 10 shown in FIG. 1 and discussed above. For some embodiments, the base layer 62 may include visible markings on a surface thereof which are configured to provide an outline for cutting an aperture in the base layer to substantially encompass a patient's wound perimeter. The base layer 62 may also include a removable film (not shown) disposed over an adhesive contact surface of the base layer 62 in order to protect the adhesive surface from contamination and to facilitate handling of the base layer 62 prior to use.

For some embodiments, the inner adhesive layer 74 and outer adhesive layer 80 may be re-securable and can be separated from a surface and then re-secured to the surface. For some embodiments, the inner adhesive layer 74 is disposed on the bottom surface of the inner cover layer 66 with an inner removable film (not shown) disposed over the inner adhesive layer. For some embodiments the inner adhesive layer 74 is disposed on the top surface of the base layer 62. For some embodiments, an outer removable film (not shown) may be disposed over the outer adhesive layer 80 prior to deployment. Removable film embodiments disposed over and protecting the inner adhesive layer 74 and outer adhesive layer 80 may have the same or similar properties to the removable films discussed above with regard to dressing 10 and may also include tab portions to facilitate removal of the films.

For some embodiments, the outer cover layer 76 may itself include an absorbent material 52, rather than serving solely as a layer intended to hold or support an absorbent material 52. For example, the maggots 48 may be placed within the wound 40, they may be surrounded by the base layer 62 and covered by the inner cover layer 66, and then the outer cover layer 76 that may be an absorbent layer 52. That outer absorbent cover layer 76 may be secured in place by an adhesive, and might be re-securable or replaceable, such that a series of top absorbent cover layers may be sequentially secured to the top of the dressing 60 (for example, by using an adhesive film or Velcro or ties, etc), each being replaced as it becomes soiled or filled with wound drainage fluid.

With regard to the above detailed description, like reference numerals used therein refer to like elements that may have the same or similar dimensions, materials and configurations. While particular forms of embodiments have been illustrated and described, it will be apparent that various modifications can be made without departing from the spirit and scope of the embodiments of the invention. Accordingly, it is not intended that the invention be limited by the forgoing detailed description.

What is claimed is:

1. A dressing for applying maggot debridement therapy to a patient's wound, comprising:
   a flexible base layer having a contact surface suitable for skin contact and configured to releasably adhere to a patient's skin;
   a flexible inner cover layer which is displaceable relative to the base layer and which has a mesh portion which includes a plurality of apertures configured to prevent passage of juvenile maggots, allow circulation of oxygen and allow wound drainage therethrough;
   an inner adhesive layer disposed between a bottom surface of the inner flexible cover layer and a top surface of the base layer which is configured to adhere the bottom surface and top surface together in a sealed junction;
   a flexible outer cover layer which is displaceable relative to the inner cover layer and which has a mesh portion; and
   an outer adhesive layer disposed between a bottom surface of the outer flexible cover layer and a top surface of the inner flexible cover layer which is configured to adhere the bottom surface of the outer cover layer and top surface of the inner cover layer together in a sealed junction.

2. The dressing of claim 1 further comprising an absorbent material disposed between the inner cover layer and outer cover layer.

3. The dressing of claim 2 wherein the absorbent material comprises gauze.

4. The dressing of claim 1 wherein substantially the entire inner cover layer comprises the mesh portion.

5. The dressing of claim 1 wherein the inner cover layer and outer cover layer have substantially the same size and shape as the size and shape of the base layer and the inner cover layer is configured to cover an outline of the base layer.

6. The dressing of claim 1 wherein the inner cover layer is secured to the base layer along an edge of the inner cover layer forming a hinged portion that allows the inner cover layer to be displaceable relative to the base layer in a hinged configuration.

7. The dressing of claim 1 wherein the outer cover layer is secured to the inner cover layer along an edge of the inner cover layer forming a hinged portion that allows the outer cover layer to be displaceable relative to the inner cover layer in a hinged configuration.

8. The dressing of claim 1 wherein the mesh portion of the inner cover layer comprises a polymer based mesh.

9. The dressing of claim 8 wherein the polymer based mesh comprises a nylon based material.

10. The dressing of claim 1 wherein the mesh portion inner cover layer has a maximum aperture size of about 25 microns to about 250 microns.

11. The dressing of claim 10 wherein the mesh portion of the inner cover layer has a maximum aperture size of about 100 microns to about 200 microns.

12. The dressing of claim 11 wherein the mesh portion of the inner cover layer has a maximum pore size of about 140 microns to about 160 microns.

13. The dressing of claim 1 wherein the mesh portion of the inner cover layer comprises substantially non-expandable apertures.

14. The dressing of claim 1 wherein the base layer, inner cover layer and outer cover layer are substantially square in shape.

15. The dressing of claim 1 wherein the base layer comprises a hypoallergenic material.

16. The dressing of claim 1 wherein the base layer comprises hydrocolloid.

17. The dressing of claim 1 wherein the base layer further comprises visible markings on a surface thereof which are configured to provide an outline for cutting an aperture in the base layer to substantially encompass a patient's wound perimeter.

18. The dressing of claim 1 further comprising a removable film disposed over the contact surface of the base layer.

19. The dressing of claim 1 wherein the base layer is sufficiently transparent or translucent to view an outline of a patient's wound through the flexible base layer.

20. The dressing of claim 1 wherein the thickness of the base layer is about 0.001 inches to about 0.25 inches.

21. The dressing of claim 1 wherein the thickness of the base layer is about 0.02 inches to about 0.1 inches.

22. The dressing of claim 1 wherein the base layer has an area of about 2 square inches to about 150 square inches.

23. The dressing of claim 1 wherein the inner adhesive layer and outer adhesive layer are re-securable and can be separated from a surface and then re-secured to the surface.

24. The dressing of claim 1 wherein the inner adhesive layer is disposed on the bottom surface of the inner cover layer.

25. The dressing of claim 1 wherein the inner adhesive layer is disposed on the top surface of the base layer.

26. The dressing of claim 1 further comprising an inner removable film disposed over the inner adhesive layer.

27. The dressing of claim 1 further comprising an outer removable film disposed over the outer adhesive layer.

28. A method of maggot debridement therapy, comprising:
   holding a base layer of a maggot debridement therapy dressing adjacent a patient's wound to approximate a profile of a wound perimeter for removing an interior section of a base layer to create an aperture in the base layer;
   removing the interior section of the flexible base layer of the maggot debridement therapy dressing to create an aperture in the base layer having a profile substantially corresponding to a profile of the patient's wound perimeter;

securing a bottom surface of the flexible base layer to the patient's tissue with the profile of the aperture of the base layer substantially aligned with the profile of the patient's wound perimeter with an adhesive layer disposed between and in contact with the bottom surface and the patient's tissue;

applying at least one maggot to the patient's wound;

removing a cover film from an adhesive layer disposed between the base layer and a cover layer having a mesh portion; and securing the cover layer to the base layer by pressing the base layer and cover layer together with the adhesive layer disposed therebetween.

* * * * *